United States Patent
Havran et al.

(10) Patent No.: US 7,342,039 B2
(45) Date of Patent: Mar. 11, 2008

(54) SUBSTITUTED INDOLE OXIMES

(75) Inventors: Lisa Marie Havran, Florence, NJ (US); John Anthony Butera, Clarksburg, NJ (US); Hassan Mahmoud Elokdah, Yardley, PA (US); Douglas John Jenkins, Collegeville, PA (US); Eric Gould Gundersen, Royersford, PA (US)

(73) Assignee: Wyeth, Madison, NJ (US)

( * ) Notice: Subject to any disclaimer, the term of this patent is extended or adjusted under 35 U.S.C. 154(b) by 464 days.

(21) Appl. No.: 10/947,846

(22) Filed: Sep. 23, 2004

(65) Prior Publication Data

US 2005/0119326 A1 Jun. 2, 2005

Related U.S. Application Data

(60) Provisional application No. 60/505,801, filed on Sep. 25, 2003.

(51) Int. Cl.
*A61K 31/404* (2006.01)
*C07D 209/04* (2006.01)

(52) U.S. Cl. ............... 514/415; 548/469; 548/490; 548/491; 548/146; 548/182; 548/215; 548/229; 548/125; 548/129; 548/132; 548/250; 548/252; 548/240; 548/243; 548/262.2; 548/364.7; 514/361; 514/364; 514/372; 514/381

(58) Field of Classification Search ............... 548/469, 548/490, 491, 146, 182, 215, 229; 514/415, 514/361, 364
See application file for complete search history.

(56) References Cited

U.S. PATENT DOCUMENTS

| | | | |
|---|---|---|---|
| 3,026,325 A | 3/1962 | Heinzelman et al. | 548/496 |
| 3,476,770 A | 11/1969 | Sherrer | 548/494 |
| 3,557,142 A | 1/1971 | Bell | 548/516 |
| 3,843,683 A | 10/1974 | Bell | 548/493 |
| 4,478,819 A | 10/1984 | Hercelin et al. | 424/457 |
| 4,736,043 A | 4/1988 | Mechel et al. | 548/492 |
| 4,851,406 A | 7/1989 | Martens et al. | 514/217.04 |
| 5,104,872 A * | 4/1992 | Tsubata et al. | 514/238.2 |
| 5,164,372 A | 11/1992 | Matsuo et al. | 514/19 |
| 5,420,289 A | 5/1995 | Musser et al. | 548/159 |
| 5,436,267 A * | 7/1995 | Komyoji et al. | 514/485 |
| 5,482,960 A | 1/1996 | Berryman | 514/414 |
| 5,502,187 A | 3/1996 | Ayer et al. | 544/117 |
| 5,541,343 A | 7/1996 | Himmelsbach et al. | 514/424 |
| 5,599,663 A | 2/1997 | Vaughan | 435/6 |
| 5,612,360 A | 3/1997 | Boyd et al. | 514/381 |
| 5,859,044 A | 1/1999 | Dow et al. | 514/419 |
| 6,048,875 A | 4/2000 | De Nanteuil et al. | 514/314 |
| 6,110,963 A | 8/2000 | Malamas | 514/443 |
| 6,166,069 A | 12/2000 | Malamas et al. | 514/469 |
| 6,232,322 B1 | 5/2001 | Malamas et al. | 514/303 |
| 6,302,837 B1 | 10/2001 | De Nanteuil et al. | 514/337 |
| 6,479,524 B1 | 11/2002 | Priepke et al. | 514/352 |
| 6,599,929 B2 | 7/2003 | Cho et al. | 514/415 |
| 6,787,556 B1 | 9/2004 | Hargreaves et al. | 514/311 |
| 6,800,645 B1 | 10/2004 | Cox et al. | 514/314 |
| 6,800,654 B2 | 10/2004 | Mayer et al. | 514/381 |
| 6,844,358 B2 | 1/2005 | Malamas et al. | 514/336 |
| 2003/0013732 A1 | 1/2003 | Elokdah | 514/301 |
| 2003/0018067 A1 | 1/2003 | Elokdah et al. | 514/469 |
| 2003/0060497 A1 | 3/2003 | Gerlach et al. | 514/414 |
| 2003/0125371 A1 | 7/2003 | Elokdah et al. | 514/419 |
| 2004/0116488 A1 | 6/2004 | Jennings et al. | 514/374 |
| 2004/0116504 A1 | 6/2004 | Elokdah et al. | 514/419 |
| 2004/0122070 A1 | 6/2004 | Jennings | 514/374 |
| 2004/0138283 A1 | 7/2004 | Jennings et al. | 514/414 |
| 2004/0204417 A1 | 10/2004 | Perez et al. | 514/249 |
| 2005/0070584 A1 | 3/2005 | Havran et al. | 514/357 |
| 2005/0070585 A1 | 3/2005 | Elokdah et al. | 514/364 |
| 2005/0070587 A1 | 3/2005 | Elokdah et al. | 514/381 |
| 2005/0070592 A1 | 3/2005 | Gundersen | 514/415 |
| 2005/0096377 A1 | 5/2005 | Hu | 514/419 |
| 2005/0113428 A1 | 5/2005 | Gopalsamy et al. | 514/364 |
| 2005/0113436 A1 | 5/2005 | Elokdah et al. | 514/411 |
| 2005/0113438 A1 | 5/2005 | Hu et al. | 514/414 |
| 2005/0113439 A1 | 5/2005 | Hu | 514/414 |
| 2005/0119296 A1 | 6/2005 | Elokdah et al. | 514/300 |
| 2005/0119327 A1 | 6/2005 | Hu | 514/414 |
| 2005/0215626 A1 | 9/2005 | Havran et al. | 514/469 |

FOREIGN PATENT DOCUMENTS

| | | |
|---|---|---|
| DE | 3147276 A1 | 11/1981 |
| DE | 43 38 770 A1 | 5/1995 |
| DE | 19543639 A1 | 5/1997 |
| DE | 19753522 | 6/1999 |
| EP | 0 414 153 A1 | 2/1991 |
| EP | 0 416 609 A2 | 3/1991 |
| EP | 0 498 396 A2 | 8/1992 |

(Continued)

OTHER PUBLICATIONS

U.S. Appl. No. 10/947,710, filed Sep. 23, 2004, Commons et al.

(Continued)

*Primary Examiner*—Golam M. M. Shameem
(74) *Attorney, Agent, or Firm*—Mabel Ng

(57) ABSTRACT

The present invention relates to substituted indole oximes and methods of using them.

28 Claims, No Drawings

FOREIGN PATENT DOCUMENTS

| | | |
|---|---|---|
| EP | 0 508 723 A1 | 10/1992 |
| EP | 0 512 570 A1 | 11/1992 |
| EP | 0 540 956 A1 | 5/1993 |
| EP | 0 564 984 A2 | 10/1993 |
| EP | 0 655 439 A2 | 5/1995 |
| EP | 0 759 434 A1 | 2/1997 |
| EP | 0 819 686 A1 | 1/1998 |
| EP | 0 822 185 A1 | 2/1998 |
| EP | 708 098 B1 | 3/1999 |
| EP | 0 916 651 A1 | 5/1999 |
| EP | 0 955 299 A1 | 11/1999 |
| EP | 1 092 716 | 4/2001 |
| EP | 1 156 045 A1 | 11/2001 |
| FR | 2 244 499 | 4/1975 |
| FR | 2 777 886 A1 | 10/1999 |
| FR | 2 799 756 A1 | 4/2001 |
| GB | 1 321 433 | 6/1973 |
| WO | WO92/18487 A1 | 10/1992 |
| WO | WO94/13637 A1 | 6/1994 |
| WO | 94/14434 A1 | 7/1994 |
| WO | 94/26738 A1 | 11/1994 |
| WO | 95/10513 A1 | 4/1995 |
| WO | WO95/29907 A1 | 11/1995 |
| WO | 96/06840 A1 | 3/1996 |
| WO | 96/21656 A1 | 7/1996 |
| WO | 96/26207 A1 | 8/1996 |
| WO | WO96/32379 A1 | 10/1996 |
| WO | 97/09308 A1 | 3/1997 |
| WO | WO97/37970 A1 | 10/1997 |
| WO | 97/43260 A1 | 11/1997 |
| WO | 97/48697 A1 | 12/1997 |
| WO | 98/08818 A1 | 3/1998 |
| WO | WO98/23155 A1 | 6/1998 |
| WO | 99/28297 A1 | 6/1999 |
| WO | 99/43651 A2 | 9/1999 |
| WO | 99/43654 A2 | 9/1999 |
| WO | 99/43672 A1 | 9/1999 |
| WO | 99/46260 A1 | 9/1999 |
| WO | WO99/43651 A2 | 9/1999 |
| WO | WO99/43654 A2 | 9/1999 |
| WO | WO99/46263 A2 | 9/1999 |
| WO | 99/50268 A1 | 10/1999 |
| WO | 99/58519 A1 | 11/1999 |
| WO | 99/61435 A1 | 12/1999 |
| WO | 00/32180 A2 | 6/2000 |
| WO | 00/35919 A1 | 6/2000 |
| WO | WO 00/37436 A1 | 6/2000 |
| WO | 00/46195 A1 | 8/2000 |
| WO | 00/46197 A1 | 8/2000 |
| WO | 00/64876 A1 | 11/2000 |
| WO | 00/64888 A1 | 11/2000 |
| WO | 01/12187 A2 | 2/2001 |
| WO | 02/030895 A1 | 4/2002 |
| WO | 02/072549 A1 | 9/2002 |
| WO | 03/000253 A1 | 1/2003 |
| WO | 03/031409 A1 | 4/2003 |
| WO | 03/068742 A1 | 8/2003 |
| WO | 03/087087 A2 | 10/2003 |
| WO | 2004/052854 A2 | 6/2004 |

OTHER PUBLICATIONS

U.S. Appl. No. 10/947,711, filed Sep. 23, 2004, Gopalsamy et al.
U.S. Appl. No. 11/208,777, filed Aug. 22, 2005, Commons et al.
U.S. Appl. No. 11/208,772, filed Aug. 22, 2005, Commons.
U.S. Appl. No. 11/208,775, filed Aug. 22, 2005, Commons et al.
Charlton, Peter, "The status of plasminogen activator inhibitor-1 as a therapeutic target," *Expert Opinion On Investigational Drugs*, May 1997, 6(5), 539-554.

Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 1422-1428.
Da Settimo, A. et al., "Reaction of indole derivatives with bromine, substitution, oxidation, and dimerization," J Org Chem, 1970, 35(8), 2546-2551.
Guzzo, P.R. et al., "Synthesis of a conformationally constrained threonin-valine dipeptide mimetic: design of a potential inhibitor of plasminogen activator inhibitor-1," *Tetrahedron Letters*, 2002 43(1), 41-43.
Malamas, M.S. et al. "Novel benzofuran and benzothiophene biphenyls as inhibitors of protein tyrosine phosphatase 1B with antihyperglycemic properties," *Journal of Medicinal Chemistry*, Apr. 6, 2000, 43(7), 1293-1310.
Aggarwal et al., "A catalytic antibody programmed for torsional activation of amide bond hydrolysis," *Chem. Eur. J.*, Jan. 25, 2003, 9(13), 3132-3142.
Ballantine, J. A., "The Chemistry of Bacteria," *Journal of the Chemical Society Abstracts*, 1957, 2222-2227.
Delgado et al., Journal of Organic Chemistry (1993), 58(10), pp. 2862-2866.
Dillard R. D. et al., "Indole Inhibitors of Human Nonpancreatic Secretory Phospholipase $A_2$ 1. Indole-3-Acetamides", *Journal of Medicinal Chemistry*, American Chemical Society, 39(26), 5119-5136.
Hipskind, P. A. et al., "Potent and selective 1,2,3-trisubstituted indole NPY Y-1 antagonists," *J Med Chem*, 1997, 40(23), 3712-3714.
Julia et al., CA 57:49169, 1962.
Malamas, M. S. et al., "Antihyperglycemic activity of new 1,2,4-oxadiazolidine-3,5-diones," *Eur. J. Med. Chem.*, 2001, 36, 31-42.
Moody et al., CA 120:298300, 1994.
Shengeliya, M. S. et al., "N-Glycosides of 5-amino-2-(ethoxycarbonyl)indole," *Zhurnal Organicheskoi Khimii*, 1986, 22(9),1868-1873.
Krishnamurti, C. et al., "Plasminogen Activator Inhibitor: A Regulator of Ancrod-Induced Fibrin Deposition in Rabbits," *Blood*, 69(3): 798-803 (Mar. 1987).
Reilly, C. et al., "Both Circulating and Clot-Bound Plasminogen Activator-1 Inhibit Endogenous Fibrinolysis in the Rat," *Arteriosclerosis and Thrombosis*, 11(5): 1276-1286 (Sep./Oct. 1991).
Carmeliet, P. et al., "Plasminogen Activator Inhibitor-1 Gene-deficient Mice," *Journal of Clinical Investigation*, 92:2756-2760 (Dec. 1993).
Rocha, E. et al., "The Relationship Between Impaired Fibrinolysis and Coronary Heart Disease," *Fibrinolysis*, 8: 294-303 (1994).
Aznar, J. et al., "Role of Plasminogen Activator Inhibitor Type 1 in the Pathogenesis of Coronary Artery Diseases," *Haemostasis* 24: 243-251 (1994).
Biemond, B. J. et al., "Thrombolysis and Reocclusion in Experimental Jugular Vein and Coronary Artery Thrombosis," *Circulation*, 91: 1175-1181 (1995).
Levi, M. et al., "Inhibition of Plasminogen Activator Inhibitor-1 Activity Results in Promotion of Endogenous Thrombolysis and Inhibition of Thrombus Experimental Thrombosis," *Circulation* 85:305-312 (1992).
Nordt, T. K. et al., "Differential Regulation by Troglitazone of Plasminogen Activator Inhibitor Type 1 in Human Hepatic and Vascular Cells," *Journal of Clinical Endocrinology and Metabolism*, 85(4):1563-1568 (2000).
Daci, E. et al., "Mice Lacking the Plasminogen Activator Inhibitor 1 are Protected from Trabecular Bone Loss Induced by Estrogen Deficiency," *Journal of Bone and Mineral Research*, 15(8):1510-1516 (Nov. 8, 2000).
Schneiderman J. et. al., "Increased type 1 plasminogen activator inhibitor gene expression in atherosclerotic human arteries," *Proc Natl Acad Sci* 89: 6998-7002.
Juhan-Vague, I. et. al., "Deficient t-PA Release and Elevated PA Inhibitor Levels in Patients with Spontaneous or Recurrent Deep Venous Thrombosis," *Thromb Haemost* 57: 67-72 (1987).
Juhan-Vague, I. et. al., "PAI-1, Obesity, Insulin Resistance and Risk of Cardiovascular Events," *Thromb Haemost* 78: 565-660 (1997).

Hamsten, A. et. al., "Plasminogen Activator Inhibitor in Plasma: Risk Factor For Recurrent Myocardial Infarction," *Lancet* 2: 3-9 (Jul. 4, 1987).

Siemens, H. J. et. al., "Course of Molecular Hemostatic Markers During and After Different Surgical Procedures," *J Clin Anesthesia* 11: 622-629 (Dec. 1999).

Koh, K. et. al., "Effects of Hormone-Replacement Therapy on Fibrinolysis in Postmenopausal Women," *N Engl J Med* 336(10): 683-690 (Mar. 6, 1997).

Ley, J. P. et al., "Hydroxy- or Methoxy-Substituted Benzaldoximes and Benzaldehyde-*O*-alkyloximes as Tyrosinase Inhibitors," *Bioorganic & Medicinal Chemistry*, 2001, 9:1879-1885.

Yoshikawa, H. et al., "Benzaldehyde O-Alkyloximes as New Plant Growth Regulators," *BioSci. Biotechnol. Biochem.*, 62(5), pp. 996-997, 1998.

Yoshikawa, H. et al., "Synthesis and Biological Activity of Benzaldehyde o-Alkyloximes as Abscisic Acid Mimics (Part I)," *BioSci. Biotechnol. Biochem.*, 56(2), pp. 256-260, 1992.

Van Dijk, J. et al., "Oxime ether derivatives, a new class of nonsteroidal antiinflammatory compounds," *J Med Chem*, 20(9), pp. 1199-1206 (Sep. 1977).

* cited by examiner

SUBSTITUTED INDOLE OXIMES

CROSS-REFERENCE TO RELATED APPLICATIONS

This application claims the benefit of U.S. Provisional Application No. 60/505,801 filed Sep. 25, 2003, the entire disclosure of which is incorporated herein by reference.

BACKGROUND

The present invention relates generally to substituted indole oximes and methods of using them.

The serine protease inhibitor PAI-1 is one of the primary inhibitors of the fibrinolytic system. The fibrinolytic system includes the proenzyme plasminogen, which is converted to the active enzyme, plasmin, by one of two tissue type plasminogen activators, t-PA or u-PA. PAI-1 is the principal physiological inhibitor of t-PA and u-PA. One of plasmin's main responsibilities in the fibrinolytic system is to digest fibrin at the site of vascular injury. The fibrinolytic system, however, is not only responsible for the removal of fibrin from circulation but is also involved in several other biological processes including ovulation, embryogenesis, intima proliferation, angiogenesis, tumorigenesis, and atherosclerosis.

Elevated levels of PAI-1 have been associated with a variety of diseases and conditions including those associated with impairment of the fibrinolytic system. For example, elevated levels of PAI-1 have been implicated in thrombotic diseases, e.g., diseases characterized by formation of a thrombus that obstructs vascular blood flow locally or detaches and embolizes to occlude blood flow downstream. (Krishnamurti, *Blood,* 69, 798 (1987); Reilly, Arteriosclerosis and Thrombosis, 11, 1276 (1991); Carmeliet, *Journal of Clinical Investigation,* 92, 2756 (1993), Rocha, *Fibrinolysis,* 8, 294, 1994; Aznar, *Haemostasis* 24, 243 (1994)). Antibody neutralization of PAI-1 activity resulted in promotion of endogenous thrombolysis and reperfusion (Biemond, *Circulation,* 91, 1175 (1995); Levi, *Circulation* 85, 305, (1992)). Elevated levels of PAI-1 have also been implicated in diseases such as polycystic ovary syndrome (Nordt, *Journal of clinical Endocrinology and Metabolism,* 85, 4, 1563 (2000)), bone loss induced by estrogen deficiency (Daci, *Journal of Bone and Mineral Research,* 15, 8, 1510 (2000)), cystic fibrosis, diabetes, chronic periodontitis, lymphomas, diseases associated with extracellular matrix accumulation, malignancies and diseases associated with neoangiogenesis, inflammatory diseases, vascular damage associated with infections, and diseases associated with increased uPA levels such as breast and ovarian cancer.

In view of the foregoing, there exists a need for the identification of inhibitors of PAI-1 activity and for methods of using the identified inhibitors to modulate PAI-1 expression or activity in a subject in order to treat disorders associated with elevated PAI-1 levels.

SUMMARY

The present invention provides substituted indole oximes and methods of using them. In certain embodiments, substituted indole oximes of the present invention include those compounds of the following formula:

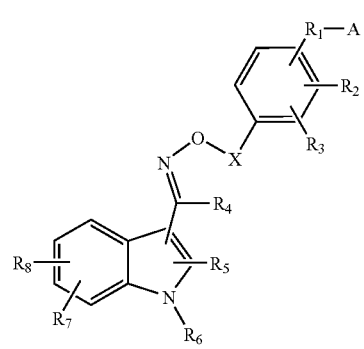

Formula 1 wherein:
R$_1$ is a direct bond to A, C$_1$-C$_4$ alkylene or —O—C$_1$-C$_4$ alkylene;

R$_2$ and R$_3$ are, independently, hydrogen, halogen, C$_1$-C$_4$ alkyl, C$_1$-C$_3$ perfluoroalkyl, —O—C$_1$-C$_3$ perfluoroalkyl, C$_1$-C$_3$ alkoxy, —OH, —NH$_2$, —NO$_2$, aryl, heteroaryl, —O(CH$_2$)$_p$-aryl, —O(CH$_2$)$_p$-heteroaryl, —NH(CH$_2$)$_p$-aryl, —NH(CH$_2$)$_p$-heteroaryl, —NH(CO)-aryl, —NH(CO)-heteroaryl, —O(CO)-aryl, —O(CO)-heteroaryl, —NH(CO)—CH=CH-aryl, or —NH(CO)—CH=CH-heteroaryl;

p is an integer from 0-6;

R$_4$ is hydrogen, C$_1$-C$_8$ alkyl, or C$_3$-C$_6$ cycloalkyl;

A is —COOH or an acid mimic;

X is C$_1$-C$_8$ alkylene, C$_3$-C$_6$ cycloalkylene, —(CH$_2$)$_m$O—, or —(CH$_2$)$_m$NH—;

m is an integer from 1-6; and

R$_5$ is hydrogen, C$_1$-C$_8$ alkyl, C$_3$-C$_6$ cycloalkyl, —CH$_2$-C$_3$-C$_6$ cycloalkyl, heteroaryl, —CH$_2$-heteroaryl, aryl, or benzyl;

R$_6$ is hydrogen, C$_1$-C$_8$ alkyl, C$_3$-C$_6$ cycloalkyl, —CH$_2$—C$_3$-C$_6$ cycloalkyl, —(CH$_2$)$_q$—CH=CH$_2$, —(CH$_2$)$_q$—CH=CH-alkyl, —(CH$_2$)$_q$—CH=C-dialkyl, —(CH$_2$)$_q$C≡CH, —(CH$_2$)$_q$C≡C-alkyl, aryl, (CH$_2$)$_q$-aryl, heteroaryl, —(CH$_2$)$_q$-heteroaryl, —CO-aryl, —CO-heteroaryl, —CO-alkyl, —SO$_2$-alkyl, —SO$_2$-aryl, or —SO$_2$-heteroaryl, q is an integer from 0 to 6;

R$_7$ and R$_8$, are, independently, hydrogen, halogen, C$_1$-C$_6$ alkyl, C$_1$-C$_6$ perfluoroalkyl, —O—C$_1$-C$_6$ perfluoroalkyl, C$_1$-C$_6$ alkoxy, —OH, —NH$_2$, —NO$_2$, —O(CH$_2$)$_n$-aryl, —O(CH$_2$)$_n$-heteroaryl, aryl, or heteroaryl; and n is an integer from 0-6.

In certain exemplary embodiments, R$_1$ is a direct bond to A or C$_1$-C$_3$ alkylene. R$_2$ may be hydrogen, halogen, C$_1$-C$_3$ alkyl, C$_1$-C$_3$ perfluoroalkyl, aryl, heteroaryl, —O—C$_1$-C$_3$ perfluoroalkyl, C$_1$-C$_3$ alkoxy, —OH, —O(CH$_2$)$_p$-aryl, —NH(CO)-aryl or —NH(CO)-heteroaryl. R$_3$ may be hydrogen, halogen, C$_1$-C$_3$ alkyl, C$_1$-C$_3$ perfluoroalkyl, aryl, heteroaryl, —O—C$_1$-C$_3$ perfluoroalkyl, C$_1$-C$_3$ alkoxy, —OH, —O(CH$_2$)$_p$-aryl, —NH(CO)-aryl or —NH(CO)-heteroaryl. R$_4$ may be hydrogen or C$_1$-C$_4$ alkyl. R$_5$ may be hydrogen, C$_1$-C$_8$ alkyl, C$_3$-C$_6$ cycloalkyl, aryl, or heteroaryl. R$_6$ may be hydrogen, C$_1$-C$_6$ alkyl, or (CH$_2$)$_q$-aryl. R$_7$ may be hydrogen, halogen, C$_1$-C$_6$ alkyl, C$_1$-C$_6$ perfluoroalkyl, —O—C$_1$-C$_6$ perfluoroalkyl, or C$_1$-C$_6$ alkoxy. R$_8$ may be hydrogen, halogen, C$_1$-C$_6$ alkyl, C$_1$-C$_6$ perfluoroalkyl, —O—C$_1$-C$_6$ perfluoroalkyl, or $C_1$-$C_6$ alkoxy. A may be —COOH or tetrazole. X may be —CH$_2$—, —CH$_2$—CH$_2$—O—, or —CH$_2$—CH$_2$—CH$_2$—O—.

$R_7$ and $R_8$ are each suitably hydrogen. $R_6$ is suitably methyl or benzyl. $R_5$ is suitably hydrogen or methyl. $R_4$ is suitably hydrogen. X is suitably —CH$_2$— or —(CH$_2$)$_3$—O—. $R_2$ and $R_3$ are each suitably hydrogen, bromo, hydroxy, 4-trifluoromethylphenyl or 4-tbutyl-phenyl-carbomylamino. Preferably one of $R_2$ and $R_3$ is hydrogen. A is suitably a bond or —CHy-. Ry is suitably CO$_2$H.

The present invention also provides, inter alia, pharmaceutically acceptable salt or ester forms of compounds of formulas 1-7.

The present invention further provides, inter alia, methods of using substituted indole oximes. In one aspect of the present invention, a therapeutically effective amount of one or more substituted indole oximes is administered to a subject in order to treat a PAI-1 related disorder, e.g., by inhibiting PAI-1 activity in the subject. PAI-1 activity is associated with a number of diseases and conditions. For example, in one embodiment of the present invention, PAI-1 activity is associated with impairment of the fibrinolytic system. In other embodiments, PAI-1 activity is associated with thrombosis, e.g., venous thrombosis, arterial thrombosis, cerebral thrombosis, and deep vein thrombosis, atrial fibrillation, pulmonary fibrosis, thromboembolic complications of surgery, cardiovascular disease, e.g., myocardial ischemia, atherosclerotic plaque formation, chronic obstructive pulmonary disease, renal fibrosis, polycystic ovary syndrome, Alzheimer's disease, or cancer.

DETAILED DESCRIPTION

A. General Overview

The present invention provides compounds that inhibit PAI-1 activity, processes for preparing such compounds, pharmaceutical compositions containing such compounds, and methods for using such compounds in medical therapies. The compounds have properties that are useful for the treatment, including the prevention and inhibition, of a wide variety of diseases and disorders involving the production and/or action of PAI-1. These include disorders resulting from impairment of the fibrinolytic system including, but not limited to, thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion and pulmonary fibrosis. Other disorders include, but are not limited to, polycystic ovary syndrome, Alzheimer's disease, and cancer.

The terms "alkyl" and "alkylene," as used herein, whether used alone or as part of another group, refer to substituted or unsubstituted aliphatic hydrocarbon chains, the difference being that alkyl groups are monovalent (i.e., terminal) in nature whereas alkylene groups are divalent and typically serve as linkers. Both include, but are not limited to, straight and branched chains containing from 1 to 12 carbon atoms, e.g. 1 to 8 carbon atoms, preferably 1 to 6 carbon atoms, more preferably 1 to 4 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to 10 carbon atoms (unless explicitly specified otherwise) and containing at least one double bond. Preferably, the alkenyl moiety has 1 or 2 double bonds. Such alkenyl moieties can exist in the E or Z conformations and the compounds of this invention include both conformations. Specifically included within the definition of "alkenyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Heteroatoms, such as O or S attached to an alkenyl should not be attached to a carbon atom that is bonded to a double bond.

The term "alkynyl", as used herein, whether used alone or as part of another group, refers to a substituted or unsubstituted aliphatic hydrocarbon chain and includes, but is not limited to, straight and branched chains having 2 to 10 carbon atoms (unless explicitly specified otherwise) and containing at least one triple bond. Preferably, the alkynyl moiety has 3 to 6 carbon atoms. In certain embodiments, the alkynyl can contain more than one triple bond and, in such cases, the alkynyl group must contain at least three carbon atoms. Specifically included within the definition of "alkynyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Heteroatoms, such as O or S attached to an alkynyl should not be attached to the carbon that is bonded to a triple bond.

The term "cycloalkyl" as used herein, whether alone or as part of another group, refers to a substituted or unsubstituted alicyclic hydrocarbon group having 3 to about 20 carbon atoms, preferably 3 to 6 carbon atoms (unless explicitly specified otherwise). Specifically included within the definition of "cycloalkyl" are those alicyclic hydrocarbon groups that are optionally substituted. For example, in certain embodiments of the present invention, the rings of the cycloalkyl can be optionally substituted by 1 to 3 groups selected from halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —NH$_2$, or —NO$_2$.

The term "aryl", as used herein, whether used alone or as part of another group, is defined as a substituted or unsubstituted aromatic hydrocarbon ring group having 5 to about 50 carbon atoms with from about 6 to about 14 carbon atoms being preferred. The "aryl" group can have a single ring or multiple condensed rings. The term "aryl" includes, but is not limited to phenyl, α-naphthyl, β-naphthyl, biphenyl, anthryl, tetrahydronaphthyl, fluorenyl, indanyl, biphenylenyl, and acenaphthenyl. Specifically included within the definition of "aryl" are those aromatic groups that are optionally substituted. Accordingly, the aryl groups described herein refer to both unsubstituted or substituted aryl groups. For example, in representative embodiments of the present invention, the, "aryl" groups are optionally substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Exemplary substituents on the aryl groups herein include alkyl, alkoxy, halo, cyano, nitro, trihalomethyl, and thioalkoxy. In certain embodiments of the present invention, the rings of the aryl groups are optionally substituted by 1 to 3 groups selected from halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —$NH_2$, —$NO_2$, —CN, aryl, —O-aryl, —NH-aryl, —NH—CO-alkyl, or —NH—CO-aryl.

As used herein, the term "heteroaryl", whether used alone or as part of another group, is defined as a substituted or unsubstituted aromatic heterocyclic ring system (monocyclic or bicyclic). Heteroaryl groups can have, for example, from about 3 to about 50 carbon atoms (unless explicitly specified otherwise) with from about 4 to about 10 being preferred. In some embodiments, heteroaryl groups are aromatic heterocyclic rings systems having about 4 to about 14 ring atoms and containing carbon atoms and 1, 2, 3, or 4 heteroatoms selected from oxygen, nitrogen or sulfur. Representative heteroaryl groups are furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Specifically included within the definition of "heteroaryl" are those aromatic heterocyclic rings that are optionally substituted with 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. In exemplary embodiments of the present invention, the rings of the heteroaryl group can be optionally substituted by 1 to 3 groups selected from halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —$NH_2$, —$NO_2$, —CN, aryl, —O-aryl, —NH-aryl, —NH—CO-alkyl, or —NH—CO-aryl.

The term "alkoxy" as used herein, refers to the group —O—$R_a$ wherein $R_a$ is an alkyl group as defined above.

Exemplary substituents on the alkyl, alkenyl, alkynyl, thioalkoxy and alkoxy groups mentioned above include, but are not limited to, halogen, —O—$C_1$-$C_6$ alkyl, —NH—$C_1$-$C_6$ alkyl, —CN, —OH, and amino groups.

The term "arylalkyl", as used herein, whether used alone or as part of another group, refers to the group —$R_a$—$R_b$, where $R_a$ is an alkyl group as defined above, substituted by $R_b$, an aryl group, as defined above. Examples of arylalkyl moieties include, but are not limited to, benzyl, 1-phenylethyl, 2-phenylethyl, 3-phenylpropyl, 2-phenylpropyl and the like.

The term "alkylheteroaryl", as used herein, whether used alone or as part of another group, refers to the group —$R_c$—$R_d$, where $R_c$ is a heteroaryl group as defined above, substituted with $R_d$, an alkyl group as defined above.

The term "heterocycle", as used herein, whether used alone or as part of another group, refers to a stable 3 to 8-member ring containing carbons atoms and from 1 to 3 heteroatoms selected from the group consisting of nitrogen, phosphorus, oxygen, and sulfur. A heterocycle of this invention can be either a monocyclic or bicyclic ring system, and can be either saturated or partially saturated. Heterocycle groups include, but are not limited to, aziridinyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl.

The term "perfluoroalkyl", as used herein, whether used alone or as part of another group, refers to a saturated aliphatic hydrocarbon having 1 to 6 carbon atoms and two or more fluorine atoms and includes, but is not limited to, straight or branched chains, such as —$CF_3$, —$CH_2CF_3$, —$CF_2CF_3$ and —$CH(CF_3)_2$.

The term "halogen" refers to chlorine, bromine, fluorine, and iodine.

In the present invention, both "q" and "n" can be 0, 1, 2, 3, 4, 5, or 6. "m" can be 1, 2, 3, 4, 5, or 6.

The term "treating" or "treatment" refers to any indicia of success in amelioration of an injury, pathology, or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" or "treatment of a PAI-1 related disorder" includes preventing the onset of symptoms in a subject that may be predisposed to a PAI-1 related disorder but does not yet experience or exhibit symptoms of the disorder (prophylactic treatment), inhibiting the symptoms of the disorder (slowing or arresting its development), providing relief from the symptoms or side-effects of the disorder (including palliative treatment), and/or relieving the symptoms of the disorder (causing regression). Accordingly, the term "treating" includes the administration of the compounds or agents of the present invention to a subject to prevent or delay, to alleviate, or to arrest or inhibit development of the symptoms or conditions associated with PAI-1 related disorders, e.g., tumor growth associated with cancer. A skilled medical practitioner will know how to use standard methods to determine whether a patient is suffering from a disease associated with enhanced levels and/or activity of PAI-1 e.g., by examining the patient and determining whether the patient is suffering from a disease known to be associated with elevated PAI-1 levels or activity or by assaying for PAI-1 levels in blood plasma or tissue of the individual suspected of suffering from a PAI-1 related disease and comparing PAI-1 levels in the blood plasma or tissue of the individual suspected of suffering from a PAI-1 related disease to PAI-1 levels in the blood plasma or tissue of a healthy individual. Increased PAI-1 levels are indicative of disease. Accordingly, the present invention provides, inter alia, methods of administering a compound of the present invention to a subject and determining levels of PAI-1 in the subject. The level of PAI-1 in the subject can be determined before and/or after administration of the compound.

In healthy individuals, PAI-1 is found at low levels in the plasma (for example, about 5-26 ng/mL), but it is elevated in many PAI-1 related disorders, including, for example, atherosclerosis (Schneiderman J. et. al, *Proc Natl Acad Sci* 89: 6998-7002, 1992) deep vein thrombosis (Juhan-Vague I, et. al, *Thromb Haemost* 57: 67-72, 1987), and non-insulin dependent diabetes mellitus (Juhan-Vague I, et. al, *Thromb Haemost* 78: 565-660, 1997). PAI-1 stabilizes both arterial and venous thrombi, contributing respectively to coronary arterial occlusion in post-myocardial infarction (Hamsten A, et. al. *Lancet* 2:3-9, 1987), and venous thrombosis following post-operative recovery from orthopedic surgery. (Siemens H J, et. al, *J Clin Anesthesia* 11: 622-629, 1999). Plasma PAI-1 is also elevated, for example, in postmenopausal women, and has been proposed to contribute to the increased incidence of cardiovascular disease in this population (Koh K et. al, *N Engl J Med* 336: 683-690, 1997).

The term "PAI-1 related disorder or disease" refers to any disease or condition that is associated with increased or enhanced expression or activity of PAI-1 or increased or enhanced expression or activity of a gene encoding PAI-1. Examples of such increased activity or expression can include one or more of the following: activity of the protein or expression of the gene encoding the protein is increased above the level of that in normal subjects; activity of the protein or expression of the gene encoding the protein is in an organ, tissue or cell where it is not normally detected in normal subjects (i.e. spatial distribution of the protein or expression of the gene encoding the protein is altered); activity of the protein or expression of the gene encoding the protein is increased when activity of the protein or expression of the gene encoding the protein is present in an organ, tissue or cell for a longer period than in a normal subjects (i.e., duration of activity of the protein or expression of the gene encoding the protein is increased). A normal or healthy subject is a subject not suffering from a PAI-1 related disorder or disease.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" refers to salts and esters that are pharmaceutically acceptable and have the desired pharmacological properties. Such salts include, for example, salts that can be formed where acidic protons present in the compounds are capable of reacting with inorganic or organic bases. Suitable inorganic salts include, for example, those formed with the alkali metals or alkaline earth metals, e.g. sodium and potassium, magnesium, calcium, and aluminum. Suitable organic salts include, for example, those formed with organic bases such as the amine bases, e.g. ethanolamine, diethanolamine, triethanolamine, trimethamine, N methylglucamine, and the like. Pharmaceutically acceptable salts can also include acid addition salts formed from the reaction of basic moieties, such as amines, in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention can be present in more than one stereoisomeric form, and the naming of such compounds is intended to include all single stereoisomers and all mixtures (whether racemic or otherwise) of such stereoisomers.

"Inhibitors," "activators," and "modulators" of expression or of activity are used to refer to inhibitory, activating, or modulating molecules, respectively, identified using in vitro and in vivo assays for expression or activity. Inhibitors of the present invention are compositions that, inhibit expression of PAI-1 or bind to, partially or totally block stimulation, decrease, prevent, delay activation, inactivate, desensitize, or down regulate the activity of PAI-1. Samples or assays comprising PAI-1 can be treated with a composition of the present invention and compared to control samples without a composition of the present invention. Control samples (untreated with compositions of the present invention) can be assigned a relative activity value of 100%. In certain embodiments, inhibition of PAI-1 is achieved when the activity value relative to the control is about 80% or less, optionally 50% or 25, 10%, 5% or 1%.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the compound.

A "therapeutically effective amount" or "pharmaceutically effective amount" means the amount that, when administered to a subject, produces effects for which it is administered. For example, a "therapeutically effective amount," when administered to a subject to inhibit PAI-1 activity, is sufficient to inhibit PAI-1 activity. A "therapeutically effective amount," when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that are associated with the targeted or suspected disease or condition. These and other routine methods allow the clinician to select patients in need of therapy using the methods and formulations of the present invention.

When any variable occurs more than one time in any constituent or in any formula, its definition in each occurrence is independent of its definition at every other occurrence. Combinations of substituents and/or variables are permissible only if such combinations result in stable compounds.

B. Substituted Indole Oximes

The present invention provides substituted indole oximes. Such compounds are preferably administered to inhibit PAI-1 expression or activity in a subject and, ultimately, to treat diseases or conditions associated with increased PAI-1 activity in a subject, e.g., a PAI-1 related disorder.

Substituted indole oximes include those compounds of the following formula:

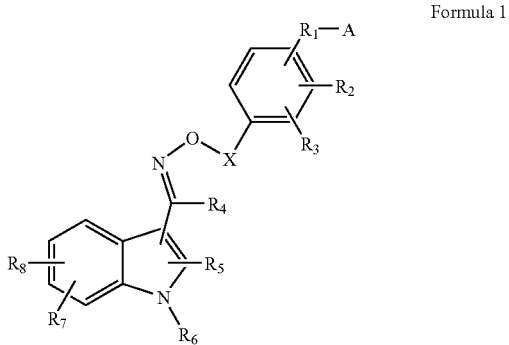

Formula 1 wherein:
$R_1$ is a direct bond to A, $C_1$-$C_4$ alkylene, or —O—$C_1$-$C_4$ alkylene;
$R_2$ and $R_3$ are, independently, hydrogen, halogen, $C_1$-$C_4$ alkyl, $C_1$-$C_3$ perfluoroalkyl, —O—$C_1$-$C_3$ perfluoroalkyl, $C_1$-$C_3$ alkoxy, —OH, —NH$_2$, —NO$_2$, aryl, heteroaryl, —O(CH$_2$)$_p$-aryl, —O(CH$_2$)$_p$-heteroaryl, —NH(CH$_2$)$_p$-aryl, —NH(CH$_2$)$_p$-heteroaryl, —NH(CO)-aryl, —NH(CO)-heteroaryl, —O(CO)-aryl, —O(CO)-heteroaryl, —NH(CO)—CH═CH-aryl, or —NH(CO)—CH═CH-heteroaryl;
p is an integer from 0-6;
$R_4$ is hydrogen, $C_1$-$C_8$ alkyl, or $C_3$-$C_6$ cycloalkyl;
A is —COOH or an acid mimic;
X is $C_1$-$C_8$ alkylene, $C_3$-$C_6$ cycloalkylene, —(CH$_2$)$_m$O—, or —(CH$_2$)$_m$NH—;
m is an integer from 1-6; and
$R_5$ is hydrogen, $C_1$-$C_8$ alkyl, $C_3$-$C_6$ cycloalkyl, —CH$_2$—$C_3$-$C_6$ cycloalkyl, heteroaryl, —CH$_2$-heteroaryl, aryl, or benzyl;

$R_6$ is hydrogen, $C_1$-$C_8$ alkyl, $C_3$-$C_6$ cycloalkyl, —CH$_2$—$C_3$-$C_6$ cycloalkyl, —(CH$_2$)$_q$—CH═CH$_2$, —(CH$_2$)$_q$—CH═CH-alkyl, —(CH$_2$)$_q$—CH═C-dialkyl, —(CH$_2$)$_q$C≡CH, —(CH$_2$)$_q$C≡C-alkyl, aryl, —(CH$_2$)$_q$-aryl, heteroaryl, —(CH$_2$)$_q$-heteroaryl, —CO-aryl, —CO-heteroaryl, —CO-alkyl, —SO$_2$-alkyl, —SO$_2$-aryl, or —SO$_2$-heteroaryl;
q is an integer from 0 to 6;
$R_7$ and $R_8$, are, independently, hydrogen, halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —NH$_2$, —NO$_2$, —O(CH$_2$)$_n$-aryl, —O(CH$_2$)$_n$-heteroaryl, aryl, or heteroaryl; and
n is an integer from 0-6.

Compounds of the present invention also include prodrugs, stereoisomers, or pharmaceutically acceptable salts or ester forms of formula 1.

Representative $R_1$ groups of formula 1 include, but are not limited to, $C_1$-$C_4$ alkylene, $C_1$-$C_3$ alkylene —O—$C_1$-$C_3$ alkylene, or —O—$C_1$-$C_4$ alkylene optionally substituted by 1 to 3 groups selected from $C_1$-$C_4$ alkyl, aryl, or benzyl.

Representative $R_2$ groups of formula 1 include, but are not limited to, —O(CH$_2$)$_p$-aryl, —O(CH$_2$)$_p$-heteroaryl, aryl, heteroaryl, —NH(CH$_2$)$_p$-aryl, —NH(CH$_2$)$_p$-heteroaryl, —NH(CO)-aryl or —NH(CO)-heteroaryl groups wherein the rings of the aryl and heteroaryl groups are optionally substituted by 1 to 3 groups selected from halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —NH$_2$, —CN or —NO$_2$. In certain embodiments, $R_2$ is hydrogen, —OH, halogen, phenyl substituted with CF3, or —NH(CO)-aryl wherein the aryl group is unsubstituted or substituted with t-butyl. In such embodiments, $R_1$, $R_3$, $R_4$, $R_5$, $R_6$, $R_7$, $R_8$, X, A, p, m, q, and n are as defined herein for formula 1.

Representative $R_3$ groups of formula 1 include, but are not limited to, —O(CH$_2$)$_p$-aryl, —O(CH$_2$)$_p$-heteroaryl, aryl, heteroaryl, —NH(CH$_2$)p-aryl, —NH(CH$_2$)$_p$-heteroaryl, NH(CO)-aryl, or —NH(CO)-heteroaryl groups wherein the rings of the aryl and heteroaryl groups are optionally substituted by 1 to 3 groups selected from halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —CN, —NH$_2$, or —NO$_2$. In certain embodiments, $R_3$ is hydrogen, —OH, halogen, phenyl substituted with CF3, or —NH(CO)-aryl wherein the aryl group is unsubstituted or substituted with t-butyl. In such embodiments, $R_1$, $R_2$, $R_4$, $R_5$, $R_6$, $R_7$, $R_8$, X, A, p, m, q, and n are as defined herein for formula 1.

Representative $R_4$ groups of formula 1 include, but are not limited to, $C_1$-$C_6$ alkyl, hydrogen, $C_3$-$C_6$ cycloalkyl, and aryl. In some preferred embodiments, $R_4$ is hydrogen. In such embodiments, $R_1$, $R_2$, $R_3$, $R_5$, $R_6$, $R_7$, $R_8$, X, A, p, m, q, and n are as defined herein for formula 1.

$R_5$ can be hydrogen, $C_1$-$C_8$ alkyl, $C_3$-$C_6$ cycloalkyl, —CH$_2$—$C_3$-$C_6$ cycloalkyl, pyridinyl, —CH$_2$-heteroaryl, aryl or benzyl. Representative $R_5$ groups of formula 1 include, but are not limited to, $C_3$-$C_6$ cycloalkyl, —CH$_2$—$C_3$-$C_6$ cycloalkyl, pyridinyl, —CH$_2$-pyridinyl, phenyl or benzyl wherein the rings of the cycloalkyl, pyridinyl, phenyl and/or benzyl groups are substituted by 1 to 3 groups selected from halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —CN, —NH$_2$, or —NO$_2$. In certain preferred embodiments, $R_5$ is hydrogen or alkyl. In such embodiments, $R_1$, $R_2$, $R_3$, $R_4$, $R_6$, $R_7$, $R_8$, X, A, p, m, q, and n are as defined herein for formula 1.

$R_6$ can be hydrogen, $C_1$-$C_8$ alkyl, $C_3$-$C_6$ cycloalkyl, —CH$_2$—$C_3$-$C_6$cycloalkyl, —(CH$_2$)$_q$CH═CH$_2$, —$(CH_2)_q$—CH=CH-alkyl, —$(CH_2)_q$—CH=C-dialkyl, —$(CH_2)_q$C≡CH, —$(CH_2)_q$C≡C-alkyl, aryl, $(CH_2)_q$-aryl, heteroaryl, —$(CH_2)_q$-heteroaryl, —CO-aryl, —CO-heteroaryl, —CO-alkyl, —$SO_2$-alkyl, —$SO_2$-aryl, or —$SO_2$-heteroaryl. Representative $R_6$ groups of formula 1 include, but are not limited to, aryl, —$(CH_2)_q$-aryl, heteroaryl, —$(CH_2)_q$-heteroaryl, —CO-aryl, —CO-heteroaryl, —CO-alkyl, —$SO_2$-alkyl, —$SO_2$-aryl, or —$SO_2$-heteroaryl wherein the rings of the aryl and/or heteroaryl groups are substituted by 1 to 3 groups selected from halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —$NH_2$, —CN or —$NO_2$. In certain preferred embodiments, $R_6$ is benzyl. In such embodiments, $R_1$, $R_2$, $R_3$, $R_4$, $R_5$, $R_7$, $R_8$, X, A, p, m, q, and n are as defined herein for formula 1.

Representative $R_7$ groups of formula 1 include, but are not limited to, —$O(CH_2)_n$-aryl, —$O(CH_2)_n$-heteroaryl, aryl, or heteroaryl wherein the rings of the aryl and/or heteroaryl groups are substituted by 1 to 3 groups selected from halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —$NH_2$, —CN or —$NO_2$. In certain preferred embodiments, $R_7$ is hydrogen or alkyl. In such embodiments, $R_1$, $R_2$, $R_3$, $R_4$, $R_5$, $R_6$, $R_8$, X, A, p, m, q, and n are as defined herein for formula 1.

Representative $R_8$ groups of formula 1 include, but are not limited to, —$O(CH_2)_n$-aryl, —$O(CH_2)_n$-heteroaryl, aryl, or heteroaryl groups that are optionally substituted by 1 to 3 groups selected from halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —$NH_2$, —CN or —$NO_2$. In certain preferred embodiments, $R_8$ is hydrogen or alkyl. In such embodiments, $R_1$, $R_2$, $R_3$, $R_4$, $R_5$, $R_6$, $R_7$, X, A, p, m, q, and n are as defined herein for formula 1.

Representative X groups of formula 1 include, but are not limited to, $C_1$-$C_6$ alkyl, $C_1$-$C_6$ branched alkyl, and —$(CH_2)_m$ wherein m is an integer from 2 to 5.

Representative A groups of formula 1 include, but are not limited to, —COOH and tetrazole.

In certain embodiments, such substituted indole oximes include the following compounds:

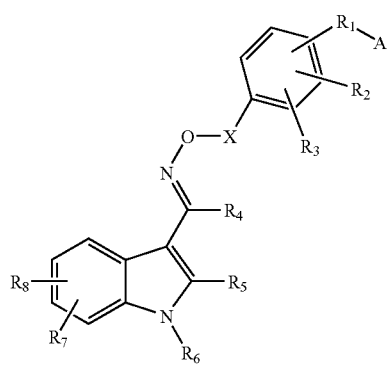

Formula 2

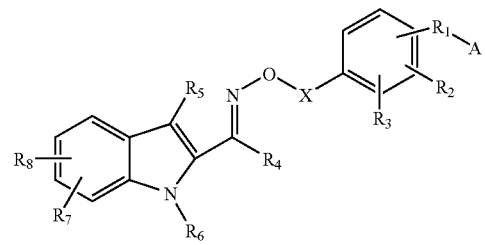

Formula 3

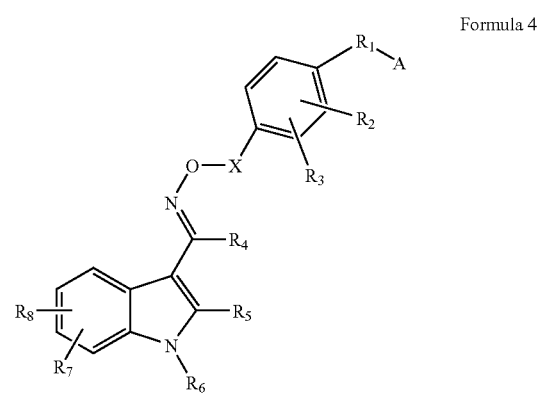

Formula 4

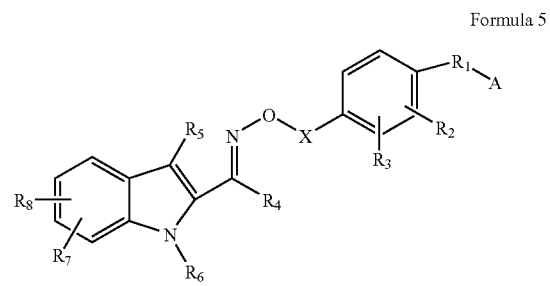

Formula 5

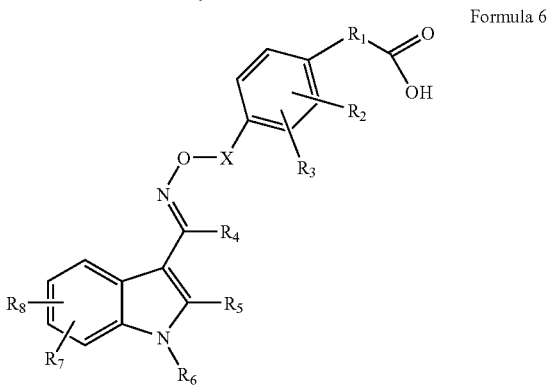

Formula 6

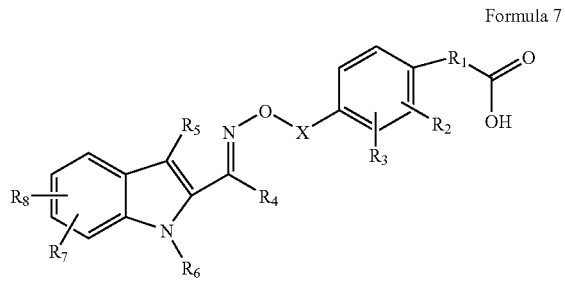

Formula 7 wherein $R_1$, $R_2$, $R_3$, $R_4$, $R_5$, $R_6$, $R_7$, $R_8$, X, A, p, m, q, and n are defined as above for Formula 1.

Exemplary substituted indole oximes of the present invention include 4-[3-({[(1E)-(1-benzyl-1H-indol-3-yl)methylidene]amino}oxy)propoxy]-2-[(4-tert-butylbenzoyl)amino]benzoic acid or a pharmaceutically acceptable salt or ester form thereof; 4-[3-({[(1E)-(1-benzyl-1H-indol-3-yl)methylidene]amino}oxy)propoxy]-2-hydroxybenzoic acid or a pharmaceutically acceptable salt or ester form thereof; 4-[({[(1E)-(1-benzyl-1H-indol-3-yl)methylidene]amino}oxy)methyl]-2-bromobenzoic acid or a pharmaceutically acceptable salt or ester form thereof; 4-[({[(1E)-(1-benzyl-1H-indol-2-yl)methylidene]amino}oxy)methyl]-2-bromobenzoic acid or a pharmaceutically acceptable salt or ester form thereof; 4-[3-({[(1E)-(1-benzyl-1H-indol-2-yl)methylidene]amino}oxy)propoxy]-2-hydroxybenzoic acid or a pharmaceutically acceptable salt or ester form thereof; 6-[3-({[(1E)-(1-benzyl-1H-indol-3-yl)methylidene]amino}oxy)propoxy]-4'-(trifluoromethyl)-1,1'-biphenyl-3-carboxylic acid or a pharmaceutically acceptable salt or ester form thereof; {4-[3-({[(1E)-(1,2-dimethyl-1H-indol-3-yl)methylidene]amino}oxy)propoxy]phenyl}acetic acid or a pharmaceutically acceptable salt or ester form thereof; 6-[3-({[(1E)-(1-benzyl-1H-indol-2-yl)methylidene]amino}oxy)propoxy]-4'-(trifluoromethyl)-1,1'-biphenyl-3-carboxylic acid or a pharmaceutically acceptable salt or ester form thereof; 2-bromo-4-[({[(1E)-(1,2-dimethyl-1H-indol-3-yl)methylidene]amino}oxy)methyl]benzoic acid or a pharmaceutically acceptable salt or ester form thereof.

The present invention also provides compositions comprising substituted indole oximes, including those compounds of formulas 1-7 or a stereoisomer or pharmaceutically acceptable salt thereof, and one or more pharmaceutically acceptable carriers, excipients, or diluents. Such compositions include pharmaceutical compositions for treating or controlling disease states or conditions associated with increased PAI-1 activity. In certain embodiments, the compositions comprise mixtures of one or more substituted indole oximes.

Certain of the compounds of formulas 1-7 contain stereogenic carbon atoms or other chiral elements and thus give rise to stereoisomers, including enantiomers and diastereomers. The present invention includes all of the stereoisomers of formulas 1-7, as well as mixtures of the stereoisomers. Throughout this application, the name of the product, where the absolute configuration of an asymmetric center is not indicated, is intended to embrace the individual stereoisomers as well as mixtures of stereoisomers.

Where an enantiomer is preferred, it can, in some embodiments, be provided substantially free of the corresponding enantiomer. Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. Methods for the preparation of preferred enantiomers are described, for example, in Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, Ind. 1972).

Exemplary salt forms of the compounds herein include, but are not limited to, sodium salts and potassium salts. Other exemplary salt forms of these compounds include, but are not limited to, those formed with pharmaceutically acceptable inorganic and organic bases known in the art. Salt forms prepared using inorganic bases include hydroxides, carbonates or bicarbonates of the therapeutically acceptable alkali metals or alkaline earth metals, such as sodium potassium, magnesium, calcium and the like. Acceptable organic bases include amines, such as benzylamine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Exemplary salts also include alkylene diamines containing up to 6 carbon atoms, such as hexamethylenediamine; cyclic saturated or unsaturated bases containing up to 6 carbon atoms, including pyrrolidine, piperidine, morpholine, piperazine and their N-alkyl and N-hydroxyalkyl derivatives, such as N-methyl-morpholine and N-(2-hyroxyethyl)-piperidine, or pyridine. Quaternary salts can also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methyl-morpholinium, N-methyl-N-(2-hydroxyethyl)-morpholinium, or N,N-dimethyl-piperidinium salt forms. These salt forms can be prepared using the acidic compound(s) of Formulas 1-7 and procedures known in the art.

Exemplary ester forms of the compounds of this invention include, but are not limited to, straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters, cycloalkyl esters, alkylaryl esters, benzyl esters, and the like. Other exemplary esters include, but are not limited to, those of the formula —COOR$_9$ wherein R$_9$ is selected from the formula:

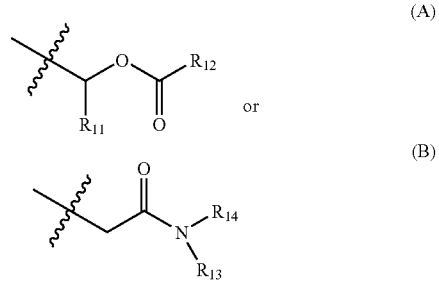

wherein $R_{11}$, $R_{12}$, $R_{13}$, $R_{14}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Acids and acid mimics, according to the invention, are defined as proton or hydrogen donating groups. Exemplary acid mimics or mimetics of the present invention include pharmaceutically useful carboxylic acids and acid mimics or mimetics known in the art, such as those described in R. Silverman, The Organic Chemistry of Drug Design and Drug Action, Academic Press (1992) and others. Exemplary acid mimics or mimetics include tetrazole, tetronic acid, acyl tetronic acid, and groups having the formula:

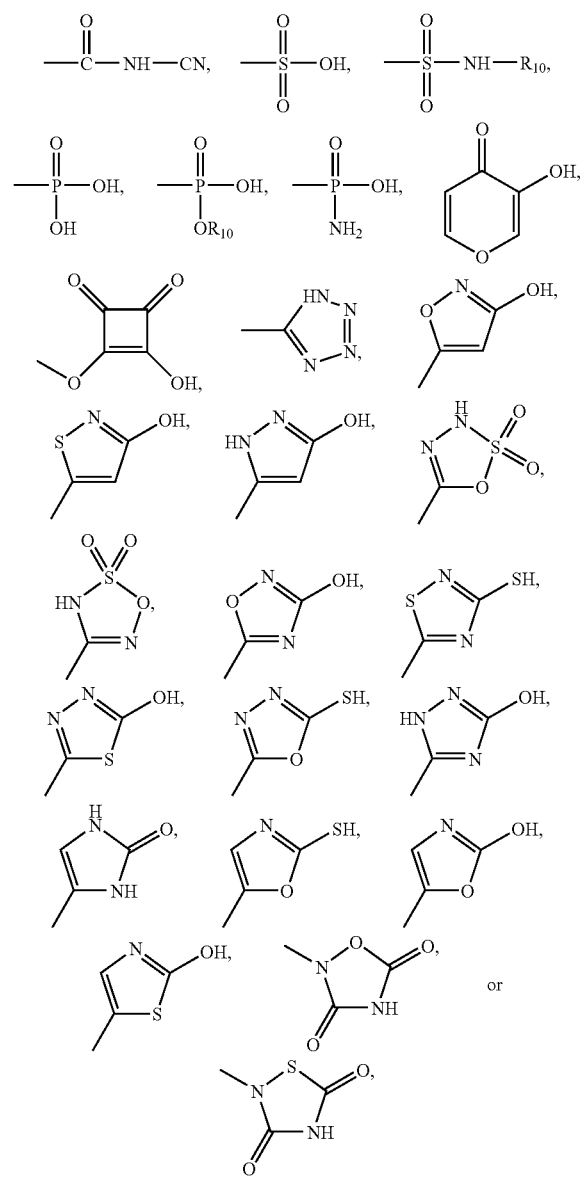

wherein $R_{10}$ is $C_1$-$C_6$ alkyl, $C_2$-$C_6$ alkenyl, $C_3$-$C_6$ cycloalkyl, —$CH_2$—($C_3$-$C_6$ cycloalkyl), $C_3$-$C_6$ cycloalkenyl, —$CH_2$— ($C_3$-$C_6$ cycloalkenyl), optionally substituted aryl or heteroaryl groups or optionally substituted aryl($C_1$-$C_6$)alkyl or heteroaryl($C_1$-$C_6$)alkyl, with the aryl and heteroaryl groups as defined herein.

Preferred compounds of the present invention inhibit PAI-1 activity. Accordingly, the compounds can be used for the treatment, including prevention, inhibition, and/or amelioration of PAI-1 related disorders in a subject, including, for example, in the treatment of noninsulin dependent diabetes mellitus, in the treatment of cardiovascular disease, and in the treatment of thrombotic events associated with coronary artery and cerebrovascular disease. Using the methods of the present invention, a skilled medical practitioner will know how to administer substituted indole oximes, including those represented by formulas 1-7, to a subject suffering from any of the diseases associated with increased PAI-1 activity or expression, e.g., diabetes or cardiovascular disease, in order to effect treatment for that disease.

In one exemplary embodiment, substituted indole oximes are administered to a subject in order to treat disease processes involving thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint or hip replacement), and peripheral arterial occlusion.

Any disease or condition that is associated with increased PAI-1 activity or expression in a subject can be treated using substituted indole oximes. Exemplary diseases and conditions include stroke, e.g., stroke associated with or resulting from atrial fibrillation; diseases associated with extracellular matrix accumulation including, but not limited to, renal fibrosis, chronic obstructive pulmonary disease, polycystic ovary syndrome, restenosis, renovascular disease, and organ transplant rejection; diseases associated with neoangiogenesis, including, but not limited to, diabetic retinopathy; Alzheimer's disease, e.g., by increasing or normalizing levels of plasmin concentration in a subject; and myelofibrosis with myeloid metaplasia, e.g., by regulating stromal cell hyperplasia and increases in extracellular matrix proteins.

The compounds of the present invention can be used to treat, for example, diabetic nephropathy and renal dialysis associated with nephropathy; malignancies or cancers, including, but not limited to, leukemia, breast cancer and ovarian cancer; tumors, including, but not limited to, liposarcomas and epithelial tumors; septicemia; obesity; insulin resistance; proliferative diseases, including, but not limited to, psoriasis; conditions associated with abnormal coagulation homeostasis; low grade vascular inflammation; cerebrovascular diseases; hypertension; dementia; osteoporosis; arthritis; respiratory diseases, such as asthma; heart failure; arrhythmia; angina, including, but not limited to, angina pectoris; atherosclerosis and sequelae; kidney failure; multiple sclerosis; osteoporosis; osteopenia; dementia; peripheral vascular disease; peripheral arterial disease; acute vascular syndromes; microvascular diseases including, but not limited to, nephropathy, neuropathy, retinopathy and nephrotic syndrome; hypertension; Type I and II diabetes and related diseases; hyperglycemia; hyperinsulinemia; malignant lesions; premalignant lesions; gastrointestinal malignancies; coronary heart disease, including, but not limited to, primary and secondary prevention of myocardial infarction, stable and unstable angina, primary prevention of coronary events, and secondary prevention of cardiovascular events; and inflammatory diseases, including, but not limited to, septic shock and the vascular damage associated with infections The compounds of the present invention can also be administered to a subject in combination with a second therapeutic agent, including, but not limited to, prothrombolytic, fibrinolytic, and anticoagulant agents, or in conjunction with other therapies, for example, protease inhibitor-containing highly active antiretroviral therapy (HAART) for the treatment of diseases which originate from fibrinolytic impairment and hyper-coagulability of HIV-1 infected patients. In certain embodiments, the compounds of the present invention can be administered in conjunction with and/or following processes or procedures involving maintaining blood vessel patency, including, but not limited to, vascular surgery, vascular graft and stent patency, organ, tissue and cell implantation and transplantation. The compounds of the present invention can also be used for the treatment of blood and blood products used in dialysis, blood storage in the fluid phase, especially ex vivo platelet aggregation. The compounds of the present invention can also be administered to a subject as a hormone replacement agent or to reduce inflammatory markers or C-reactive protein. The compounds can be administered to improve coagulation homeostasis, to improve endothelial function, or as a topical application for wound healing, e.g., the prevention of scarring. The compounds of the present invention can be administered to a subject in order to reduce the risk of undergoing a myocardial revascularization procedure. The present compounds can also be added to human plasma during the analysis of blood chemistry in hospital settings to determine the fibrinolytic capacity thereof. In certain embodiments, the compounds of the present invention can be used as imaging agents for the identification of metastatic cancers.

C. Synthesis of Substituted Indole Oximes

Compounds of the present invention can be prepared by those skilled in the art of organic synthesis employing conventional methods that utilize readily available reagents and starting materials. Representative compounds of the present invention can be prepared using the following synthetic schemes. In the following synthetic schemes, $R_1$, $R_2$, $R_3$, $R_4$, $R_5$, $R_7$, $R_8$, X, and A are selected from the groups defined above. The skilled practitioner will know how to make use of variants of these process steps, which in themselves are well known in the art.

Representative substituted indole oximes of the present invention can be prepared using schemes 1-3:

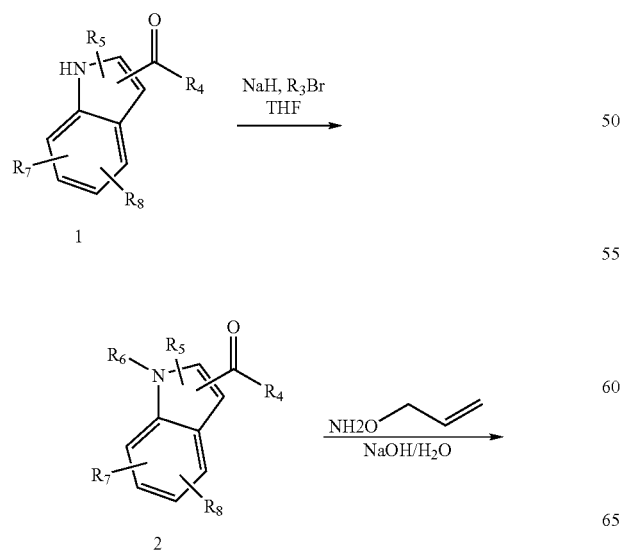

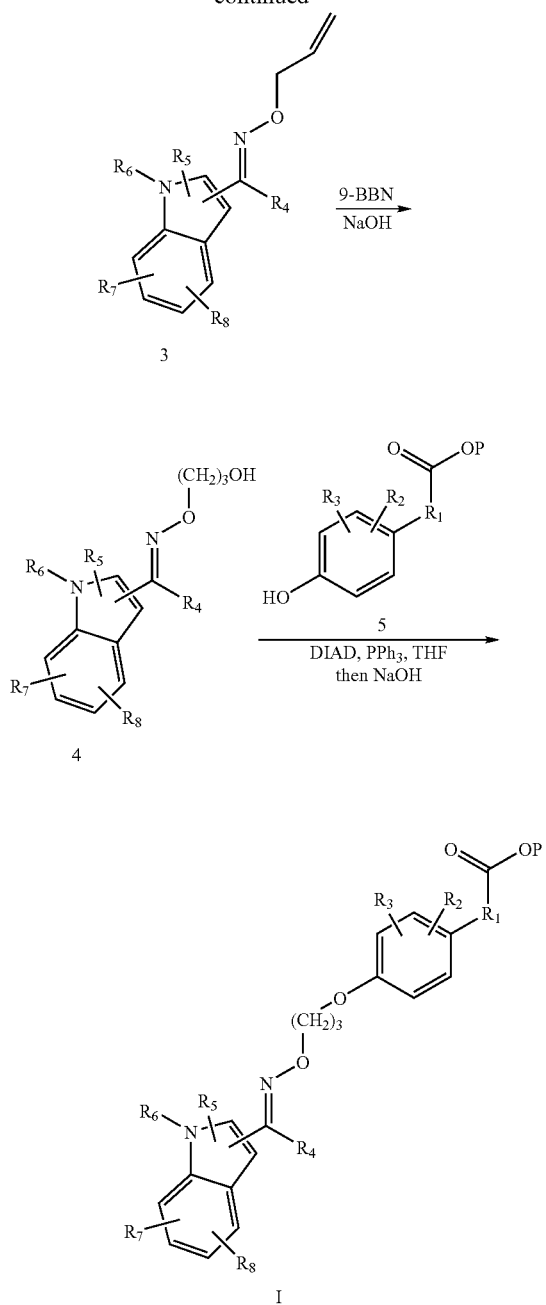

As shown in Scheme 1, indole 1 can be protected on nitrogen by deprotonation with base like sodium hydride followed by quenching of the anion with an alkylating agent. Aldehyde 2 can be reacted with O-allyl hydroxylamine hydrochloride with a base such as sodium hydroxide in a solvent mixture like ethanol/water to yield allyl oxime 3. Allyl oxime 3 can be reacted with a boron reagent like 9-BBN in a solvent like THF to give alcohol 4. Alcohol 4 can be reacted with hydroxy benzoic acid ester 5 under Mitsunobu conditions with triphenyl phosphine and a lower alkyl azodicarboxylate like diisopropyl azodicarboxylate followed by saponification of the ester moiety can furnish the corresponding acid derivatives I (when X=$(CH_2)_3$O).

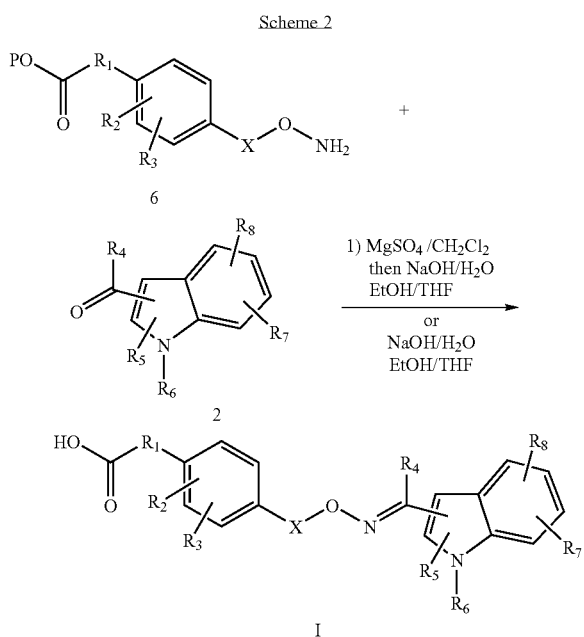

Alternatively in Scheme 2, aldehyde 2 can be coupled with the properly O-substituted hydroxyl amine 6 either in the presence of a dehydrating agent such as magnesium sulfate followed by saponification or by treatment under basic conditions to give acid derivatives I.

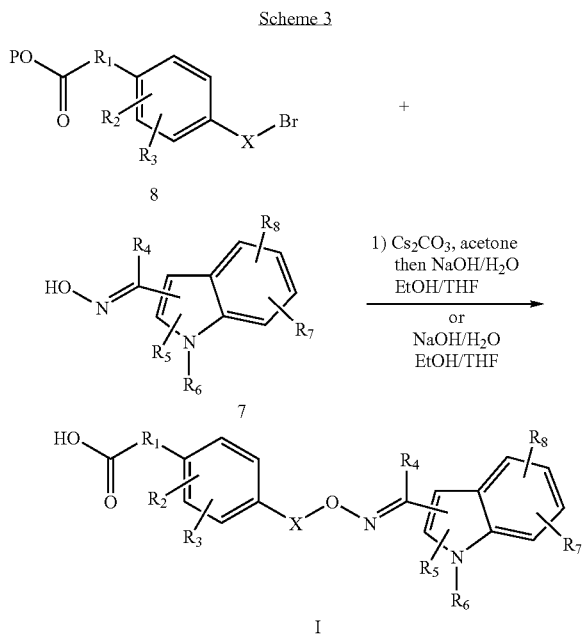

Compounds can also be prepared (as shown in Scheme 3) by coupling of the oxime 7 (prepared according to conditions similar to those in Scheme I) with bromide 8 either in presence of a base like cesium carbonate in a solvent like acetone followed by saponification or by treatment under basic conditions to give acid derivatives I.

D. Substituted Indole Oximes as Pharmaceutical Compositions

The present invention provides substituted indole oximes as pharmaceuticals. In a preferred embodiment, the indole oximes are formulated as pharmaceuticals to treat diseases associated with increased PAI-1 activity, e.g., by inhibiting PAI-1 activity in a subject.

In general, substituted indole oximes can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection). Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols. In some embodiments of the present invention, substituted indole oximes suitable for use in the practice of this invention will be administered either singly or in combination with at least one other compound of this invention. Substituted indole oximes suitable for use in the practice of the present invention can also be administered with at least one other conventional therapeutic agent for the disease being treated.

Aqueous suspensions of the invention can contain a substituted aryl oxime in admixture with excipients suitable for the manufacture of aqueous suspensions. Such excipients can include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions can be formulated by suspending a substituted aryl oxime in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of substituted aryl oxime in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol. The formulations of commends can be presented in unit-dose or multi-dose sealed containers, such as ampules and vials.

Injection solutions and suspensions can be prepared from sterile powders, granules, and tablets of the kind previously described.

Substituted indole oximes suitable for use in the practice of this invention can be administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 10% w of the substituted aryl oxime, preferably 0.00001% w to 1% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethylcellulose; and gums including arabic and tragacanth; as well as proteins such as gelatin and collagen. If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The substituted indole oximes of the present invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The substituted indole oximes of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" is intended to include the active ingredient in combination with an encapsulating material as a formulation, with or without other carriers. For example, the compounds of the present invention can also be delivered as microspheres for slow release in the body. In one embodiment, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention, e.g., anti-atherosclerotic medicaments.

In another embodiment, the compounds of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compound into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

In other cases, the preferred preparation can be a lyophilized powder which may contain, for example, any or all of the following: 1 mM-50 mM histidine, 0.1%-2% sucrose, 2%-7% mannitol, at a pH range of 4.5 to 5.5, that is combined with buffer prior to use.

A pharmaceutical composition of the invention can optionally contain, in addition to a substituted aryl oxime, at least one other therapeutic agent useful in the treatment of a disease or condition associated with increased PAI-1 activity.

The pharmaceutical compositions are generally formulated as sterile, substantially isotonic and in full compliance with all Good Manufacturing Practice (GMP) regulations of the U.S. Food and Drug Administration.

E. Determining Dosage Regimens for Substituted Indole Oximes

The present invention provides methods of inhibiting PAI-1 activity in a subject for the treatment of diseases and conditions associated with increased PAI-1 activity using substituted indole oximes. In an exemplary embodiment of the present invention, a skilled practitioner will treat a subject having a disease associated with elevated PAI-1 levels and/or activity with a compound of the present invention.

For treatment purposes, the compositions or compounds disclosed herein can be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). The pharmaceutical formulations of the present invention can be administered, for example, one or more times daily, 3 times per week, or weekly. In an exemplary embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to alleviate one or more symptoms or detectable conditions associated with increased PAI-1 activity. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response). In alternative embodiments, an "effective amount" or "effective dose" of the biologically active agent(s) can simply inhibit or enhance one or more selected biological activity(ies) correlated with a disease or condition, as set forth above, for either therapeutic or diagnostic purposes.

The actual dosage of biologically active agents will of course vary according to factors such as the extent of exposure and particular status of the subject (e.g., the subject's age, size, fitness, extent of symptoms, susceptibility factors, etc), time and route of administration, as well as other drugs or treatments being administered concurrently. Dosage regimens can be adjusted to provide an optimum prophylactic or therapeutic response. By "therapeutically effective dose" herein is meant a dose that produces effects for which it is administered. More specifically, a therapeutically effective dose of the compound(s) of the invention preferably alleviates symptoms, complications, or biochemical indicia of diseases associated with increased PAI-1 activity. The exact dose will depend on the purpose of the treatment, and will be ascertainable by one skilled in the art using known techniques (see, e.g., Lieberman, Pharmaceutical Dosage Forms (Vols. 1-3, 1992); Lloyd, 1999, The Art, Science, and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

In an exemplary embodiment of the present invention, unit dosage forms of the compounds are prepared for standard administration regimens. In this way, the composition can be subdivided readily into smaller doses at the physicians direction. For example, unit dosages can be made up in packeted powders, vials or ampoules and preferably in capsule or tablet form. The active compound present in these unit dosage forms of the composition can be present in an amount of, for example, from about one gram to about fifteen grams or more, for single or multiple daily administration, according to the particular need of the patient. By initiating the treatment regimen with a minimal daily dose of about one gram, the blood levels of PAI-1 and the patients symptomatic relief analysis can be used to determine whether a larger or smaller dose is indicated. Effective administration of the compounds of this invention can be given at an oral dose of from about 0.1 mg/kg/day to about 1,000 mg/kg/day. Preferably, administration will be from about 10/mg/kg/day to about 600 mg/kg/day, more preferably from about 25 to about 200 mg/kg/day, and even more preferably from about 50 mg/kg/day to about 100 mg/kg/day. In some embodiments, a daily dosage of from about 1 mg/kg to about 250 mg/kg is provided.

In certain embodiments, the present invention is directed to prodrugs of compounds of formulas 1-7. The term "prodrug," as used herein, means a compound that is convertible in vivo by metabolic means (e.g. by hydrolysis) to a compound of formula 1-15. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., *Journal of Drug Delivery Reviews,* 8:1-38(1992), Bundgaard, *J. of Pharmaceutical Sciences,* 77:285 et seq. (1988); and Higuchi and Stella (eds.) Prodrugs as Novel Drug Delivery Systems, American Chemical Society (1975).

F. Kits

After a pharmaceutical comprising a substituted aryl oxime has been formulated in a suitable carrier, it can be placed in an appropriate container and labeled for treatment of a PAI-1 related disorder, e.g., leukemia. Additionally, another pharmaceutical comprising at least one other therapeutic agent useful in the treatment of the PAI-1 related disorder can be placed in the container as well and labeled for treatment of the indicated disease. Alternatively, a single pharmaceutical comprising a substituted aryl oxime and at least one other therapeutic agent useful in the treatment of a PAI-1 related disorder can be placed in an appropriate container and labeled for treatment. For administration of pharmaceuticals comprising substituted indole oximes and of pharmaceuticals comprising, in a single pharmaceutical, substituted indole oximes and at least one other therapeutic agent useful in the treatment of a PAI-related disorder, such labeling would include, for example, instructions concerning the amount, frequency and method of administration. Similarly, for administration of multiple pharmaceuticals provided in the container, such labeling would include, for example, instructions concerning the amount, frequency and method of administration of each pharmaceutical.

EXAMPLES

Example 1

Synthesis of 4-[3-({[(1E)-(1-Benzyl-1H-indol-3-yl)methylidene]amino}oxy)-propoxy]-2-[(4-tert-butyl-benzoyl)amino]benzoic acid Step 1: To a solution of 4-nitro-anthranilic acid (2.200 g, 10.9 mmol, 1 eq) in benzene/methanol (4/1) (100 mL) was added TMSCHN$_2$ (2M in hexanes) (12 mL, 24 mmol, 2.2 eq). The reaction was stirred at room temperature for 30 minutes and then concentrated in vacuo. The residue was purified by flash chromatography using ethyl acetate/hexanes (20/80) to afford 4-nitro-anthranilic acid methyl ester (1.841 g, 86%) as a bright yellow solid. $^1$H NMR (300 MHz, CDCl$_3$); δ 8.00 (d, 1H), 7.50 (d, 1H), 7.40 (dd, 1H), 3.92 (s, 3H).

Step 2: To a solution of 4-nitro-anthranilic acid methyl ester (5.060 g, 25.8 mmol) in CH$_2$Cl$_2$ (200 mL) was added triethylamine (8 mL) and 4-tert-butyl benzoyl chloride and the reaction was stirred overnight at rt. It was then poured into brine, extracted with ethyl acetate, dried over MgSO$_4$ and concentrated in vacuo. The residue was purified by flash chromatography using ethyl acetate/hexanes (20/80) to afford 2-(4-tert-butyl-benzoylamino)-4-nitro-benzoic acid methyl ester (1.841 g, 86%) as a yellow solid. mp=146.0-148.4° C.; mass spectrum (-ES, M-H) m/z 355. $^1$H NMR (400 MHz, DMSO-d$_6$); δ 11.60 (bs, 1H), 9.35 (d, 1H), 8.20 (d, 1H), 8.02 (dd, 1H), 7.90 (d, 2H), 7.64 (d, 2H), 3.95 (s, 3H), 1.36 (s, 9H). Elemental analysis: Calcd. for C$_{19}$H$_{20}$N$_2$O$_5$: C, 64.04; H, 5.66; N, 7.86. Found: C, 64.04; H, 5.79; N, 7.76.

Step 3: To a Parr shaker bottle was added 10% Pd/C (0.346 g) then ethyl acetate (50 mL) followed by 2-(4-tert-butyl-benzoylamino)-4-nitro-benzoic acid methyl ester (3.041 g, 8.53 mmol) as a solution in ethyl acetate (200 mL). The reaction was hydrogenated overnight, filtered through celite and silica washing with ethyl acetate and concentrated in vacuo. The residue was purified by flash chromatography using ethyl acetate/hexanes (20/80) to afford 4-amino-2-(4-tert-butyl-benzoylamino)-benzoic acid methyl ester (2.122 g, 76%) as a yellow solid.

Step 4: To a solution of afford 4-amino-2-(4-tert-butyl-benzoylamino)-benzoic acid methyl ester (0.711 g, 2.18 mmol) in trifluoroacetic acid cooled to 0° C. was added NaNO$_2$ (0.182 g, 2.64 mmol, 1.21 eq) as a solution in water (4 mL) and the reaction was stirred 5 minutes. It was then added dropwise to 30% solution of H$_2$SO$_4$ (50 mL) at 65° C. and stirred for 15 minutes. It was extracted with ethyl acetate, dried over MgSO$_4$ and concentrated in vacuo. The residue was purified by flash chromatography using ethyl acetate/hexanes (20/80) to afford 2-(4-tert-butyl-benzoylamino)-4-hydroxy-benzoic acid methyl ester (0.508, 71%) as a white solid. mp=146.0-148.4° C.; mass spectrum (-ES, M-H) m/z 326. $^1$H NMR (400 MHz, DMSO-d$_6$); δ 11.95 (bs, 1H), 10.60 (bs, 1H), 8.26 (d, 1H), 7.88 (m, 3H), 7.62 (d, 2H), 6.58 (dd, 1H), 3.85 (s, 3H), 1.32 (s, 9H). Elemental analysis: Calcd. for C$_{19}$H$_{21}$NO$_4$: C, 69.71; H, 6.47; N, 4.28. Found: C, 69.20; H, 6.54; N, 4.17.

Step 5: To a solution of 1H-indole-3-carbaldehyde (25.0g, 172 mmol) in tetrahydrofuran (500 mL) cooled to 0° C. with an ice-bath and under an inert atmosphere was slowly added sodium hydride (4.96 g, 207 mmol), such that the temperature of the mixture remained less that 5° C. After complete addition, the mixture was allowed to stir at 0° C. for 15 minutes. To the mixture was added benzyl bromide (35.4 g, 207 mmol). The ice bath was removed and the mixture was allowed to warm to room temperature over 1.5 hours. The mixture was then partitioned between brine and ethyl acetate. The layers were separated and the aqueous layer was extracted with two additional portions of ethyl acetate. The combined organics were dried over anhydrous magnesium sulfate, filtered and concentrated under reduced pressure. The resulting red solids were dissolved in methylene chloride and the solution was filtered through a plug of silica gel. The filtrate was concentrated under reduced pressure until a precipitate began to form. The product was crystallized out of the solution by the addition of an eight-fold volume of hexane. The red-tinted solid was isolated by vacuum filtration, and the process was repeated one additional time to give 1-benzyl-1H-indole-3-carbaldehyde (38.8 g, 96%) as an off-white powder. $^1$H NMR (400 MHz, CDCl$_3$); δ 9.98 (s, 1H), 8.32 (m, 1H), 7.71 (s, 1H), 7.34 (m, 6H), 7.18 (m, 2H), 5.36 (s, 2H).

Step 6: To a solution of 1-benzyl-1H-indole-3-carbaldehyde (1.086 g, 4.61 mmol) in 4:1 ethanol:2.5 M NaOH solution (16 mL) was added O-allyl hydroxylamine hydrochloride hydrate(0.768 g, 7.17 mmol). The reaction mixture was heated to reflux for 30 minutes and allowed to cool back down to room temperature. The reaction mixture was concentrated to a small volume and the pH of the mixture was then adjusted to 7 using 2 M hydrochloric acid. The mixture was extracted with ethyl acetate. The combined organics were washed with brine, dried over anhydrous magnesium sulfate, filtered and concentrated under reduced pressure. The crude oil was purified by flash chromatography through silica gel using ethyl acetate/hexanes (10/90) to give 1-benzyl-1H-indole-3-carbaldehyde O-allyl-oxime (0.176 g, 88%) as a colorless oil. $^1$H NMR (400 MHz, CDCl$_3$); δ 8.30(s, 1H), 8.15 (m, 1H), 7.24 (m, 7H), 7.10 (d, 2H), 6.10 (m, 1H), 5.30 (m, 4H), 4.68 (d, 2H).

Step 7: To a solution of 1-benzyl-1H-indole-3-carbaldehyde O-allyl-oxime (2.965 g, 10.2 mmol) in tetrahydrofuran (50 mL) cooled to 0° C. was added 9-BBN (0.5 M in THF)(50.0 mL, 25.0 mmol). The reaction was stirred at 0° C. for 1 hour and then warmed to room temperature over 30 minutes. Hydrogen peroxide (12 mL) was carefully added followed by a 10% NaOH solution (20 mL) and stirring continued at room temperature for 25 minutes. The reaction was quenched by the addition of saturated sodium bisulfite and extracted with ethyl acetate. The combined organic were washed with saturated sodium bisulfite and brine, dried over MgSO$_4$ and concentrated in vacuo. The residue was purified by flash chromatography through silica gel using ethyl acetate/hexanes (10/90 to 40/60) to give 1-benzyl-1H-indole-3-carbaldehyde O-(3-hydroxy-propyl)-oxime (1.298 g, 41%) as a white solid. mp=76.4-77.7° C.; mass spectrum (+ES, M+H) m/z 309. $^1$H NMR (400 MHz, CDCl$_3$); δ 8.33 (s, 1H), 8.01 (d, 1H), 7.92 (s, 1H), 7.49 (d, 1H), 7.22 (m, 7H), 5.44 (s, 2H), 4.47 (t, 1H), 4.13 (t, 2H), 3.52 (q, 2H), 1.82 (m, 2H). Elemental analysis: Calcd. for C$_{19}$H$_{20}$N$_2$O$_2$: C, 74.0; H, 6.54; N, 9.08. Found: C, 73.74; H, 6.46; N, 8.95.

Step 8: To a solution of 2-(4-tert-butyl-benzoylamino)-4-hydroxy-benzoic acid methyl ester (0.313 g, 0.96 mmol) in tetrahydrofuran (14 mL) was added 1-benzyl-1H-indole-3-carbaldehyde O-(3-hydroxy-propyl)-oxime (0.303 g, 0.98 mmol) and triphenyl phosphine (0.327 g, 1.26 mmol). The reaction was cooled to 0° C., diisopropyl azodicarboxylate (0.240 mL, 1.22 mmol) was added and warmed to room temperature overnight. It was poured into brine and extracted with ethyl acetate. The combined organics were washed with brine, dried over MgSO$_4$ and concentrated in vacuo. The residue was purified by flash chromatography using ethyl acetate/hexanes (10/90) to afford 4-[3-({[(1E)-(1-benzyl-1H-indol-3-yl)methylidene]amino}oxy)-propoxy]-2-[(4-tert-butylbenzoyl)amino]benzoic acid methyl ester (0.328g, 55 %) as a white solid. (+ES, M+H) m/z 618. $^1$H NMR (400 MHz, DMSO-d$_6$); δ 11.95 (s, 1H), 8.42 (d, 1H), 8.38 (s, 1H), 7.98 (m, 2H), 7.88 (d, 2H), 7.82 (s, 1H) 7.62 (d, 2H), 7.47 (d, 1H), 7.29 (m, 2H), 7.21 (m, 4H), 7.08 (m, 1H), 6.81 (dd, 1H), 5.43 (s, 2H), 4.24 (m, 4H), 3.88 (s, 3H), 2.19 (m, 2H), 1.32 (s, 9H). Elemental analysis: Calcd. for C$_{38}$H$_{39}$N$_3$O$_5$: C, 73.88; H, 6.36; N, 6.8. Found: C, 73.40; H, 6.44; N, 6.37.

Step 9: To a solution of 4-[3-({[(1E)-(1-benzyl-1H-indol-3-yl)methylidene]amino}oxy)-propoxy]-2-[(4-tert-butyl-benzoyl)amino]benzoic acid methyl ester (0.229 g, 0.47 mmol) in ethanol/water/tetrahydrofuran (8/3/1) was added 2.5 N NaOH (6 mL, 15 mmol) and the reaction was heated at reflux for 45 minutes until all starting material was gone. It was cooled to room temperature, concentrated to a small volume in vacuo and acidified to pH 1 with 2N HCl solution. It was extracted with ethyl acetate, dried over magnesium sulfate and concentrated in vacuo. The residue was purified by flash chromatography using ethyl acetate/hexanes (10/90 to 20/80) to the title compound (0.200 g, 70%) as an off-white solid. mp=180.9-182.5° C. mass spectrum (+ES, M+H) m/z 604. $^1$H NMR (400 MHz, DMSO-d$_6$); δ 13.40 (bs, 1H), 12.40 (bs, 1H), 8.65 (d, 1H), 8.39 (s, 1H), 7.98 (d, 2H), 7.87 (d, 2H), 7.82 (s, 1H) 7.60 (d, 2H), 7.48 (d, 1H), 7.30 (m, 2H), 7.2-2 (m, 4H), 7.09 (m, 1H), 6.78 (dd, 1H), 5.42 (s, 2H), 4.26 (t, 2H), 4.22 (t, 2H), 2.20 (m, 2H), 1.31 (s, 9H) Elemental analysis: Calcd. for C$_{37}$H$_{37}$N$_3$O$_5$: C, 73.61; H, 6.18; N, 6.96. Found: C, 72.91; H, 6.22; N, 6.70.

Example 2

Synthesis of 4-[3-({[(1E)-(1-Benzyl-1H-indol-3-yl) methylidene]amino}oxy)-propoxy]-2-hydroxybenzoic acid Step 1: 4-[3-({[(1E)-(1-Benzyl-1H-indol-3-yl)methylidene]amino}oxy)-propoxy]-2-hydroxybenzoic acid methyl ester (0.327 g, 71%) was prepared from 1-benzyl-1H-indole-3-carbaldehyde O-(3-hydroxy-propyl)-oxime and 4-hydroxy phenyl acetic acid methyl ester using a procedure similar to step 8 of example 1. mp=100.3-101.5° C.; mass spectrum (+ES, M+H) m/z 459. $^1$H NMR (400 MHz, DMSO-d$_6$); δ 10.71 (bs, 1H), 8.36 (s, 1H), 7.98 (d, 1H), 7.82 (s, 1H), 7.70 (d, 1H), 7.49 (d, 1H), 7.30 (m, 2H), 7.21 (m, 4H), 7.09 (m, 1H), 2H), 5.43 (s, 2H), 4.22 (t, 2H), 4.17 (t, 2H), 3.75 (s, 3H), 2.13 (m, 2H). Elemental analysis: Calcd. for C$_{27}$H$_{26}$N$_2$O$_5$: C, 70.73; H, 5.72; N, 6.11. Found: C, 70.10; H, 5.42; N, 5.92.

Step 2: The title compound (0.108 g, 51%) was prepared from 4-[3-(1-benzyl-1H-indol-3-ylmethyleneaminooxy)-propoxy]-2-hydroxy-benzoic acid methyl ester using a procedure similar to step 9 of example 1. mp=182.0-183.4° C.; mass spectrum (+ES, M+H) m/z 445. $^1$H NMR (400 MHz, DMSO-d$_6$); δ 13.6 (bs, 1H), 11.50 (bs, 1H), 8.37 (s, 1H), 7.98 (d, 1H), 7.83 (s, 1H), 7.68 (d, 1H), 7.49 (d, 1H), 7.30 (m, 2H), 7.21 (m, 4H), 7.09 (m, 1H), 6.51 (m, 2H), 4.43 (s, 2H), 4.23 (t, 2H), 4.17 (t, 2H), 2.13 (m, 2H). Elemental analysis: Calcd. for C$_{26}$H$_{24}$N$_2$O$_5$: C, 70.26; H, 5.44; N, 6.30. Found: C, 69.83; H, 5.33; N, 6.26.

Example 3

Synthesis of 4-[({[(1E)-(1-Benzyl-1H-indol-3-yl) methylidene]amino}oxy)methyl]-2-bromobenzoic acid Step 1: To a solution of 2-bromo-4-methyl-benzoic acid (5.50 g, 25.6 mmol) in methanol (250 mL) was added concentrated sulfuric acid (1 mL). The reaction mixture was heated to reflux overnight (approximately 16 hours), allowed to cool to room temperature and then concentrated to approximately ¼ volume under reduced pressure. The residue was then partitioned between water and ethyl acetate, the layers were separated and the aqueous layer was extracted with one additional portion of ethyl acetate. The combined organics were washed one time with saturated sodium bicarbonate solution, dried over anhydrous magnesium sulfate, filtered through a plug of silica gel and concentrated under reduced pressure. 2-Bromo-4-methyl-benzoic acid methyl ester was obtained as an oil (4.95 g, 85%). To a solution of this oil (2.50 g, 10.9 mmol) in carbon tetrachloride (100 mL) was added N-bromosuccinimide (2.04 g, 11.5 mmol) and benzoylperoxide (0.106 g, 0.44 mmol). The reaction mix was heated to reflux. After approximately 1 hour, the reaction mixture became colorless. At this time the heat was removed to allow the mixture to cool to room temperature and the mixture was filtered. The filtrate was concentrated under reduced pressure. The crude mixture was purified by HPLC (40% methylene chloride in hexane) to give 2-bromo-4-bromomethyl-benzoic acid methyl ester (1.50 g, 45%) as a white powder. $^1$H NMR (400 MHz, CDCl$_3$); δ 7.75 (d, 1H), 7.66 (s, 1H), 7.35 (d, 1H), 4.39 (s, 2H), 3.90 (s, 3H).

Step 2: 1-Benzyl-1H-indole-3-carbaldehyde oxime (1.752 g, 60%) was prepared from 1-benzyl-1H-indole-3-carbaldehyde and hydroxylamine hydrochloride using a procedure similar to Step 6 of example 1. $^1$H NMR (400 MHz, DMSO-d$_6$); δ 11.30 (s, 1H), 8.40 (s, 1H), 7.88 (d, 1H), 7.80 (s, 1H), 7.50 (d, 1H), 7.22 (m, 7H), 5.50 (s, 2H).

Step 3: To a solution of 2-bromo-4-bromomethyl-benzoic acid methyl ester (0.50g, 1.62 mmol) and 1-benzyl-1H-indole-3-carbaldehyde oxime (0.43 g, 1.70 mmol) in acetone (50 mL) was added cesium carbonate (2.12 g, 6.49 mmol). The mixture was heated to reflux for 6 hours and allowed to cool back to room temperature. The mixture was partitioned between ethyl acetate and brine and the layers were then separated. The aqueous layer was extracted with one additional portion of ethyl acetate. The organics were combined, dried over anhydrous magnesium sulfate, filtered and concentrated under reduced pressure. The crude material was purified by flash chromatography through silica gel using ethyl acetate/hexanes (0/100 gradient to 20/80) to give an off-white solid. This solid was recrystallized one time from ethyl acetate/hexanes (1/6) to give 4-[({[(1E)-(1-benzyl-1H-indol-3-yl)methylidene]amino}oxy)methyl]-2-bromobenzoic acid methyl ester (0.26 g, 34%) as off-white crystals. $^1$H NMR (400 MHz, CDCl$_3$); δ 8.12 (s, 1H), 7.76 (m, 4H), 7.68 (s, 1H), 7.35 (d, 1H), 7.28 (m, 3H), 7.23 (m, 2H), 7.11 (d, 2H), 5.33 (s, 2H), 5.27 (s, 2H), 3.90 (s, 3H).

Step 4: To a solution of 4-[({[(1E)-(1-benzyl-1H-indol-3-yl)methylidene]amino}oxy)methyl]-2-bromobenzoic acid methyl ester (0.20 g, 0.42 mmol) in 10/5/3 tetrahydrofuran/ethanol/water (12 mL) was added 2.5 M sodium hydroxide solution (2 mL). This mixture was heated to reflux for 3 hours and then allowed to cool back to room temperature. The mixture was concentrated to approximately ¼ volume and partitioned between ethyl acetate and water. The aqueous layer was acidified to approximately pH 1 using 1 N hydrochloric acid. The layers were then separated. The aqueous layer was extracted with one additional portion of ethyl acetate. The organics were combined, dried over anhydrous magnesium sulfate, filtered and concentrated under reduced pressure. The crude material was recrystallized one time from ethyl acetate/hexanes (1/10) to give the title compound (0.15 g, 75%) as a white powder. mp=107-109° C. $^1$H NMR (400 MHz, DMSO-d$_6$); δ 13.33 (bs, 1H), 8.42 (s, 1H), 7.92 (s, 1H), 7.90 (d, 1H), 7.73 (d, 1H), 7.71 (s, 1H), 7.52 (d, 1H), 7.44 (d, 1H), 7.23 (m, 7H), 5.52 (s, 2H), 5.28 (s, 2H). Mass spec; (ES+) m/z 462.9, (ES−) m/z 463.2. Elemental analysis; Calculated for C$_{24}$H$_{19}$BrN$_2$O$_3$: C, 62.22; H, 4.13; N, 6.05. Found: C, 61.61; H, 4.03; N, 5.82.

Example 4

Synthesis of 4-[({[(1E)-(1-Benzyl-1H-indol-2-yl)methylidene]amino}oxy)methyl]-2-bromobenzoic acid Step 1: To a solution of 2-bromo-4-bromomethyl-benzoic acid methyl ester (0.40 g, 1.30 mmol) in acetonitrile (15 mL) was added N-hydroxyphthalimide (0.23 g, 1.40 mmol) and N,N-diisopropylethylamine (0.34 g, 2.60 mmol). This mixture was allowed to stir at room temperature for 3.5 hours. The mixture was filtered and the filtrate was concentrated under reduced pressure. The crude material was purified by flash chromatography through silica gel using methylene chloride to give 2-bromo-4-(1,3-dioxo-1,3-dihydro-isoindol-2-yloxymethyl)-benzoic acid methyl ester (0.42 g, 84%) as a white solid. $^1$H NMR (400 MHz, CDCl$_3$); δ 7.82 (m, 3H), 7.75 (m, 2H), 7.57 (d, 1H), 7.25 (s, 1H), 5.20 (s, 2H), 3.92 (s, 3H).

Step 2: To a solution of 2-bromo-4-(1,3-dioxo-1,3-dihydro-isoindol-2-yloxymethyl)-benzoic acid methyl ester (0.40 g, 1.02 mmol) in methylene chloride (15 mL) cooled to 0° C. was added methyl hydrazine (0.087 g, 1.88 mmol). After a few minutes the ice bath was removed and the mixture was allowed to stir at room temperature for 2 hours. The mixture was filtered and the filtrate was concentrated under reduced pressure. The crude material was purified by flash chromatography through silica gel using ethyl acetate/methylene chloride (0/100 gradient to 6/94) to give 4-aminooxymethyl-2-bromo-benzoic acid methyl ester (0.25 g, 94%) as a colorless oil. $^1$H NMR (400 MHz, CDCl$_3$); δ 7.79 (d, 1H), 7.66 (s, 1H), 7.32 (d, 1H), 4.67 (s, 2H), 3.92 (s, 3H).

Step 3: To a solution of 1H-indole-2-carboxylic acid ethyl ester (1.89 g, 10.0 mmol) and benzylbromide (1.71 g, 10.0 mmol) in acetone (50 mL) was added cesium carbonate (3.26 g, 10.0 mmol). The mixture was heated to reflux overnight and then allowed to cool back to room temperature. The mixture was partitioned between ethyl acetate and brine and the layers were then separated. The aqueous layer was extracted with one additional portion of ethyl acetate. The organics were combined, dried over anhydrous magnesium sulfate, filtered and concentrated under reduced pressure. The crude material was purified by flash chromatography through silica gel using ethyl acetate/hexanes (0/100 gradient to 6/94) to give 1-benzyl-1H-indole-2-carboxylic acid ethyl ester (2.38 g, 85%) as a white solid. $^1$H NMR (400 MHz, CDCl$_3$); δ 7.68 (d, 1H), 7.37-7.11 (m, 7H), 7.02 (d, 2H), 5.82 (s, 2H), 4.30 (q, 2H), 1.33 (t, 3H).

Step 4: This compound was produced by modifications of the methods used by Murakami, et.al. (Tetrahedron, 1997, 53, 1593-1606) starting with 1-benzyl-1H-indole-2-carboxylic acid ethyl ester (1.50 g, 5.37 mmol) and lithium aluminum hydride (0.61 g, 16.1 mmol). The crude (1-benzyl-1H-indol-2-yl)-methanol (1.22 g, 96%) was a white powder which did not require further purification. $^1$H NMR (400 MHz, CDCl$_3$); δ 7.62 (d, 1H), 7.27-7.10 (m, 7H), 6.99 (d, 2H), 6.52 (s, 1H), 5.44 (s, 2H), 4.69 (s, 2H).

Step 5: This compound was produced by modifications of the methods used by Murakami, et. al. (Tetrahedron, 1997, 53, 1593-1606) starting with (1-benzyl-1H-indol-2-yl)-methanol (1.13 g, 4.76 mmol) and manganese dioxide (5.6 g). The crude material was purified by flash chromatography through silica gel using diethyl ether/hexanes (0/100 gradient to 10/90) to give 1-benzyl-1H-indole-2-carbaldehyde (0.47 g, 42%) as an off-white solid. $^1$H NMR (400 MHz, CDCl$_3$); δ 79.90 (s, 1H), 7.76 (d, 1H), 7.37 (s, 2H), 7.33 (s, 1H), 7.25-7.16 (m, 4H), 7.08 (d, 2H), 5.83 (s, 2H).

Step 6: To a solution of 4-aminooxymethyl-2-bromobenzoic acid methyl ester (0.21 g, 0.81 mmol) and 1-benzyl-1H-indole-2-carbaldehyde (0.19 g, 0.81 mmol) in 10/5/3 tetrahydrofuran/ethanol/water (18 mL) was added 2.5 M sodium hydroxide solution (3 mL). This mixture was heated to reflux for 3 hours and then allowed to cool back to room temperature. The mixture was concentrated to approximately 1/4 volume and partitioned between ethyl acetate and water. The aqueous layer was acidified to approximately pH 1 using 1 N hydrochloric acid. The layers were then separated. The aqueous layer was extracted with one additional portion of ethyl acetate. The organics were combined, dried over anhydrous magnesium sulfate, filtered and concentrated under reduced pressure. The crude material was purified by flash chromatography through silica gel using ethyl acetate/hexanes (20/80 with 1% formic acid) to give 4-[({[(1E)-(1-benzyl-1H-indol-2-yl)methylidene]amino}oxy)methyl]-2-bromobenzoic acid (0.19 g, 51%) as an off-white powder. mp=148-149° C. $^1$H NMR (400 MHz, DMSO-$d_6$); δ 13.35 (bs, 1H), 8.51 (s, 1H), 7.66 (m, 2H), 7.60 (d, 1H), 7.48 (d, 1H), 7.34 (d, 1H), 7.21-7.15 (m,4H), 7.06 (t, 1H), 6.93 (s, 1H), 6.90 (d, 2H), 5.70 (s, 2H), 5.14 (s, 2H). Mass spec; (ES+) m/z 462.9, (ES−) m/z 461.3. Elemental analysis; Calculated for $C_{24}H_{19}BrN_2O_3$: C, 62.22; H, 4.13; N, 6.05. Found: C, 62.07; H, 4.38; N, 5.88.

Example 5

Synthesis of 4-[3-({[(1E)-(1-Benzyl-1H-indol-2-yl)methylidene]amino}oxy)propoxy]-2-hydroxybenzoic acid Step 1: This compound was produced by modifications of the methods used *J. Med. Chem.*, 1991, 34, 1071 starting with N-hydroxyphthalimide (10.0 g, 61.3 mmol), 1,3-dibromo-propane (24.8 g, 123 mmol) and triethylamine (12.4 g, 123 mmol). The crude material was purified by flash chromatography through silica gel using chloroform to give 2-(3-bromo-propoxy)-isoindole-1,3-dione (9.30 g, 53%) as a white powder. $^1$H NMR (400 MHz, CDCl$_3$); δ 7.81 (m, 2H), 7.73 (m, 2H), 4.34 (t, 2H), 3.68 (t, 2H), 2.28 (m, 2H).

Step 2: To a solution of 2,4-dihydroxy-benzoic acid methyl ester (1.42 g, 8.45 mmol) and 2-(3-bromo-propoxy)-isoindole-1,3-dione (2.00 g, 7.04 mmol) ) in acetone (50 mL) was added cesium carbonate (6.88 g, 21.1 mmol). The mixture was heated to reflux for 3 hours and allowed to cool back to room temperature. The mixture was partitioned between ethyl acetate and brine and the layers were then separated. The aqueous layer was extracted with two additional portions of ethyl acetate. The organics were combined, dried over anhydrous magnesium sulfate, filtered and concentrated under reduced pressure. The crude material was purified by flash chromatography through silica gel using chloroform to give 4-[3-(1,3-dioxo-1,3-dihydro-isoindol-2-yloxy)-propoxy]-2-hydroxy-benzoic acid methyl ester (0.76 g, 30%) as a white solid. $^1$H NMR (400 MHz, CDCl$_3$); δ 10.86 (s, 1H), 7.76 (m, 2H), 7.68 (m, 3H), 6.40 (m, 2H), 4.35 (t, 2H), 4.21 (t, 2H), 3.85 (s, 3H), 2.20 (m, 2H).

Step 3: This compound was produced using similar methods as those used in Step 2, example 4, starting with 4-[3-(1,3-dioxo-1,3-dihydro-isoindol-2-yloxy)-propoxy]-2-hydroxy-benzoic acid methyl ester (0.42 g, 1.12 mmol) and methyl hydrazine (0.087 g, 1.88 mmol). The crude material was purified by flash chromatography through silica gel using ethyl acetate/chloroform (10/90) to give 4-(3-aminooxy-propoxy)-2-hydroxy-benzoic acid methyl ester (0.26 g, 96%) as a white solid. $^1$H NMR (400 MHz, CDCl$_3$); δ 7.51 (d, 1H), 6.23 (s, 1H), 6.21 (d, 1H), 3.85 (t, 2H), 3.69 (s, 3H), 3.62 (t, 2H), 1.86 (m, 2H).

Step 4: To a solution of 4-(3-aminooxy-propoxy)-2-hydroxy-benzoic acid methyl ester (0.17 g, 0.69 mmol) and 1-benzyl-1H-indole-2-carbaldehyde (0.16 g, 0.69 mmol) in methylene chloride (10 mL) was added anhydrous magnesium sulfate (0.04 g). The mixture was allowed to stir at ambient temperature overnight, then heated to reflux for 1 hour and allowed to cool back to ambient temperature. The mixture was filtered and the filtrate was concentrated under reduced pressure. The crude material was purified by flash chromatography through silica gel using ethyl acetate/hexanes (0/100 gradient to 20/80) to give 4-[3-({[(1E)-(1-benzyl-1H-indol-2-yl)methylidene]amino}oxy)propoxy]-2-hydroxybenzoic acid methyl ester (0.11 g, 36%) as a white solid. $^1$H NMR (400 MHz, CDCl$_3$); δ 10.94 (s, 1H), 8.16 (s, 1H), 7.70 (d, 1H), 7.63 (d, 1H), 7.28-7.17 (m, 5H), 7.11 (t, 1H), 7.00 (d, 2H), 6.78 (s, 1H), 6.41 (s, 1H), 6.39 (d, 1H), 5.72 (s, 2H), 4.21 (t, 2H), 3.98 (t, 2H), 3.89 (s, 3H), 2.03 (m, 2H).

Step 5: This compound was produced using similar methods as those used in Step 5, example 3, starting with 4-[3-({[(1E)-(1-benzyl-1H-indol-2-yl)methylidene]amino}oxy)propoxy]-2-hydroxybenzoic acid methyl ester (0.104 g, 0.23 mmol) and 2.5 M sodium hydroxide solution (3 mL). The crude material was purified by flash chromatography through silica gel using ethyl acetate/hexanes (10/90 with 1% formic acid gradient to 20/80 with 1% formic acid) followed by recrystallization one time from methylene chloride/hexanes to give 4-[3-({[(1E)-(1-benzyl-1H-indol-2-yl)methylidene]amino}oxy)propoxy]-2-hydroxybenzoic acid (0.063 g, 62%) as a white solid. mp=175-176° C. (dec). $^1$H NMR (400 MHz, DMSO-$d_6$); δ 11.50 (bs, 1H), 8.41 (s, 1H), 7.68 (d, 1H), 7.60 (d, 1H), 7.48 (d, 1H), 7.25-7.16 (m, 5H), 7.06 (t, 1H), 6.99 (d, 2H), 6.91 (s, 1H), 6.47 (d, 1H), 6.44 (s, 1H), 5.75 (s, 2H), 4.18 (t, 2H), 4.05 (t, 2H), 2.00 (m, 2H). Mass spec; (ES+) m/z 445.1, (ES−) m/z 443.4. Elemental analysis; Calculated for $C_{26}H_{24}N_2O_5$: C, 70.26; H, 5.44; N, 6.30. Found: C, 69.86; H, 5.43; N, 6.09.

Example 6

Synthesis of 6-[3-({[(1E)-(1-Benzyl-1H-indol-3-yl)methylidene]amino}oxy)propoxy]-4'-(trifluoromethyl)-1,1'-biphenyl-3-carboxylic acid.

Step 1: To a solution of 4-hydroxy-benzoic acid methyl ester (10.0 g, 65.7 mmol) in acetonitrile (110 mL), which has been cooled to at least −5° C. using an ice/acetone bath under a nitrogen atmosphere, was slowly added tetrafluoroboric acid (54% by wt. in diethyl ether, 6.35 g, 72.3 mmol) while maintaining the temperature less than −5° C. After complete addition, a solution of N-bromosuccinimide (12.9 g, 72.3 mmol) dissolved in acetonitrile (55 mL) was slowly added to the reaction mixture such that the temperature did not rise above 10° C. The ice bath was then removed and the reaction mixture was allowed to warm to room temperature and stir for 3 hours. The reaction was quenched by the addition of saturated sodium bisulfite solution until the yellow color was gone. The reaction mixture was extracted with two portions of diethyl ether. The combined organics were washed with one portion of brine, dried over anhydrous magnesium sulfate, filtered and concentrated under reduced pressure. The crude material was purified by flash chromatography through silica gel using methylene chloride/hexanes (gradient from 80/20 to 100/0) to give 3-bromo-4-hydroxy-benzoic acid methyl ester (13.5 g, 89%) as a white powder. ¹H NMR (400 MHz, CDCl₃); δ 8.18 (s, 1H), 7.91 (d, 1H), 7.04 (d, 1H), 6.02 (bs, 1H), 3.88 (s, 3H).

Step 2: To a solution of 3-bromo-4-hydroxy-benzoic acid methyl ester (4.50 g, 19.5 mmol) and 4-trifluoromethylbenzene boronic acid (4.07 g, 21.4 mmol) in dioxane (75 mL) was added 2 M potassium bicarbonate solution (29.2 mL, 58.4 mmol) and a second portion of dioxane (75 mL, 150 mL total volume added). This mixture was then degassed by bubbling dry nitrogen through the mixture for 5 minutes. After degassing, [1,1'-bis(diphenylphosphino)-ferrocene] dichloro palladium (II), complex 1:1 with dichloromethane (DPPF; 0.40 g, 0.49 mmol) was added and the reaction mixture was stirred at ambient temperature for 1 hour. The mixture was then heated to reflux for 5 hours, allowed to cool back to ambient temperature for 14 hours and then refluxed for an additional 5 hours. After cooling back to ambient temperature, the mixture was partitioned between 1 M hydrochloric acid (100 mL) and ethyl acetate. The layers were separated and the aqueous layer was adjusted to pH 3. The aqueous layer was extracted with two additional portions of ethyl acetate. The organics were combined, dried over anhydrous magnesium sulfate, filtered through Celite and concentrated under reduced pressure. The crude material was purified by flash chromatography through silica gel using diethyl ether/hexanes (0/100 gradient to 20/80) to give 6-hydroxy-4'-trifluoromethyl-biphenyl-3-carboxylic acid methyl ester (3.40 g, 76%) as a white powder. ¹H NMR (400 MHz, DMSO-d₆); δ 10.76 (s, 1H), 7.87 (s, 1H), 7.84 (d, 1H), 7.76 (s, 4H), 7.06 (d, 1H), 3.79 (s, 3H).

Step 3: To a solution of 6-hydroxy-4'-trifluoromethyl-biphenyl-3-carboxylic acid methyl ester (1.20 g, 4.05 mmol) and 1,3-dibromopropane (4.09 g, 20.3 mmol) in acetone (125 mL) was added potassium carbonate (2.80 g, 20.3 mmol). The reaction mixture was heated to reflux for 3 hours and allowed to cool back down to room temperature. The mixture was partitioned between ethyl acetate and brine, and the layers were separated. The aqueous layer was extracted with one additional portion of ethyl acetate. The organics were combined, dried over anhydrous magnesium sulfate, filtered and concentrated under reduced pressure. The crude oil was purified by flash chromatography through silica gel using ethyl acetate/hexanes (0/100 gradient to 9/91) to give 6-(3-bromo-propoxy)-4'-trifluoromethyl-biphenyl-3-carboxylic acid methyl ester (1.23 g, 73%) as a white powder. ¹H NMR (400 MHz, CDCl₃); δ 8.03 (d, 1H), 7.99 (s, 1H), 7.61 (AA'BB', 4H), 7.02 (d, 1H), 4.18 (t, 2H), 3.88 (s, 3H), 3.43 (t, 2H), 2.23 (m, 2H).

Step 4: To a solution of 6-(3-bromo-propoxy)-4'-trifluoromethyl-biphenyl-3-carboxylic acid methyl ester (0.30 g, 0.72 mmol) and 1-benzyl-1H-indole-3-carbaldehyde oxime (0.18 g, 0.72 mmol) in 10/5/3 tetrahydrofuran/ethanol/water (18 mL) was added 2.5 M sodium hydroxide solution (3 mL). This mixture was heated to reflux for 2.5 hours and then allowed to cool back to room temperature. The mixture was partitioned between ethyl acetate and water. The aqueous layer was acidified to approximately pH 1 using 1 N hydrochloric acid. The layers were then separated. The aqueous layer was extracted with one additional portion of ethyl acetate. The organics were combined, dried over anhydrous magnesium sulfate, filtered and concentrated under reduced pressure. The crude material was purified by flash chromatography through silica gel using ethyl acetate/hexanes (20/80 with 1% formic acid) to give 6-[3-({[(1E)-(1-benzyl-1H-indol-3-yl)methylidene]amino}oxy)propoxy]-4'-(trifluoromethyl)-1,1'-biphenyl-3-carboxylic acid (0.041 g, 10%) as a white solid. mp=193-194° C. ¹H NMR (400 MHz, DMSO-d₆); δ 8.24 (s, 1H), 7.94 (d, 1H), 7.90-7.86 (m, 3H), 7.78-7.74 (m, 5H), 7.40 (d, 1H), 7.25-7.11 (m, 7H), 5.43 (s, 2H), 4.26 (t, 2H), 4.23 (t, 2H), 2.49 (m, 2H). Mass spec; (ES+) m/z 5.73.1 (ES−) m/z 571.5. Elemental analysis; Calculated for C₃₃H₂₇F₃N₂O₄: C, 69.22; H, 4.75; N, 4.89. Found: C, 68.62; H, 4.93; N, 4.81.

Example 7

Synthesis of {4-[3-({[(1E)-(1,2-Dimethyl-1H-indol-3-yl)methylidene]amino}oxy)propoxy]phenyl}acetic acid Step 1: This compound was produced using similar methods as those used Step 3, example 6, starting with (4-hydroxy-phenyl)-acetic acid methyl ester (5.00 g, 30.1 mmol), 1,3-dibromopropane (24.3 g, 120 mmol) and cesium carbonate (40.3 g, 120 mmol). The crude oil was purified by flash chromatography through silica gel using ethyl acetate/hexanes (0/100 gradient to 20/80) to give [4-(3-Bromopropoxy)-phenyl]-acetic acid methyl ester (7.10 g, 82%) as a faint-yellow oil. ¹H NMR (400 MHz, DMSO-d₆); δ 7.15 (d, 2H), 6.87 (d, 2H), 4.03 (t, 2H), 3.63 (t, 2H), 3.58 (s, 3H), 3.57 (s, 2H), 2.21 (m, 2H).

Step 2: This compound was produced by modifications of the methods used in *J. Org. Chem.*, 1987, 52, 104-109, starting with 1-methyl-1H-indole-3-carbaldehyde (5.00 g, 31.4 mmol) and iodomethane (26.7 g, 187 mmol). The crude material was purified by flash chromatography through silica gel using ethyl acetate/hexanes (10/90 gradient to 30/70) to give 5.10 g (75%) of a yellow solid. ¹H NMR (400 MHz, CDCl₃); δ 10.06 (s, 1H), 8.23 (m, 1H), 7.27-7.22 (m, 3H), 3.59 (s, 3H), 2.56 (s, 3H).

Step 3: This compound was produced using similar methods as those used in Step 3, example 3, starting with 1,2-dimethyl-1H-indole-3-carbaldehyde (0.67 g, 3.89 mmol), hydroxylamine hydrochloride (0.44 g, 6.38 mmol) and sodium hydroxide (0.95 g, 23.7 mmol). The product was used without further purification. Isolated 0.73 g (99%) of a tan solid. ¹H NMR (400 MHz, DMSO-d₆); δ 9.88 (s, 1H), 8.23 (s, 1H), 8.10 (d, 1H), 7.54 (d, 1H), 7.32-7.22 (m, 2H), 3.86 (s, 3H).

Step 4: To a solution [4-(3-bromo-propoxy)-phenyl]-acetic acid methyl ester (0.47 g, 1.64 mmol) and 1,2-dimethyl-1H-indole-3-carbaldehyde oxime (0.32 g, 1.73 mmol) in 10/5/3 tetrahydrofuran/ethanol/water (21 mL) was added 2.5 M sodium hydroxide solution (6 mL). This mixture was heated to reflux for 2.5 hours and then allowed to cool back to room temperature. The mixture was partitioned between ethyl acetate and water. The aqueous layer was acidified to approximately pH 5 using 1 N hydrochloric acid. The layers were then separated. The aqueous layer was extracted with one additional portion of ethyl acetate. The organics were combined, dried over anhydrous magnesium sulfate, filtered and concentrated under reduced pressure. The crude material was purified by flash chromatography through silica gel using ethyl acetate/hexanes (20/80 with 1% formic acid) to give {4-[3-({[(1E)-(1,2-dimethyl-1H-indol-3-yl)methylidene]amino}oxy)propoxy]phenyl}acetic acid (0.30 g, 48%) as a white solid. mp=106.5-107.5° C. ¹H NMR (400 MHz, DMSO-d₆); δ 12.20 (bs, 1H), 8.45 (s, 1H), 7.95 (d, 1H), 7.43 (d, 1H), 7.16 (t, 1H), 7.14 (d, 2H), 7.07 (t, 1H), 6.88 (d, 2H), 4.23 (t, 2H), 4,09 (t, 2H), 3.67 (s, 3H), 3.46 (s, 2H), 2.47 (s, 3H), 2.13 (m, 2H). Mass spec; (ES+) m/z 381.2 Elemental analysis; Calculated for C₂₂H₂₄N₂O₄: C, 69.46; H, 6.36; N, 7.36. Found: C, 69.25; H, 6.23; N, 7.27.

Example 8

Synthesis of 6-[3-({[(1E)-(1-Benzyl-1H-indol-2-yl)methylidene]amino}oxy)propoxy]-4'-(trifluoromethyl)-1,1'-biphenyl-3-carboxylic acid Step 1: This compound was produced using similar methods as those used in Step 1, example 4, starting with 6-(3-bromo-propoxy)-4'-trifluoromethyl-biphenyl-3-carboxylic acid methyl ester (0.60 g, 1.46 mmol), N-hydroxyphthalimide (0.30 g, 1.86 mmol) and N,N-diisopropylethylamine (0.36 g, 2.88 mmol). The crude material was purified by flash chromatography through silica gel using methylene chloride to give 6-[3-(1,3-dioxo-1,3-dihydro-isoindol-2-yloxy)-propoxy]-4'-trifluoromethyl-biphenyl-3-carboxylic acid methyl ester (0.50 g, 70%) as a white solid. $^1$H NMR (400 MHz, DMSO-d$_6$); δ 8.01 (dd, 1H), 7.88 (d, 1H), 7.84 (s, 4H), 7.74 (s, 4H), 7.31 (d, 1H), 4.31 (t, 2H), 4.22 (t, 2H), 3.82 (s, 3H), 2.09 (m, 2H).

Step 2: This compound was produced using similar methods as those used in Step 2, example 4, starting with 6-[3-(1,3-dioxo-1,3-dihydro-isoindol-2-yloxy)-propoxy]-4'-trifluoromethyl-biphenyl-3-carboxylic acid methyl ester (0.50 g, 1.00 mmol) and methyl hydrazine (0.087 g, 1.88 mmol). The crude material was purified by flash chromatography through silica gel using ethyl acetate/methylene chloride (2/98 gradient to 8/92) to give 6-(3-aminooxy-propoxy)-4'-trifluoromethyl-biphenyl-3-carboxylic acid methyl ester (0.34 g, 92%) as a white solid.

Step 3: This compound was produced using similar methods as those used in Step 6, example 4, starting with 6-(3-aminooxy-propoxy)-4'-trifluoromethyl-biphenyl-3-carboxylic acid methyl ester (0.25 g, 0.68 mmol) and 1-benzyl-1H-indole-2-carbaldehyde (0.16 g, 0.68 mmol). The crude material was purified by recrystallizing two times from ethyl acetate/hexanes followed by HPLC (82% acetonitrile in 0.1% trifluoroacetic acid solution) and one final recrystallization from ethyl acetate/hexanes to give 6-[3-({[(1E)-(1-benzyl-1H-indol-2-yl)methylidene]amino}oxy)propoxy]-4'-(trifluoromethyl)-1,1 '-biphenyl-3-carboxylic acid (0.21 g, 54%) as a white solid. mp=196-197° C. $^1$H NMR (400 MHz, DMSO-d$_6$); δ 12.80 (bs, 1H), (s, 1H), 7.96 (dd, 1H), 7.88 (d, 1H), 7.74 (AA'BB', 4H), 7.60 (d, 1H), 7.46 (d, 1H), 7.22-7.16 (m, 4H), 7.12 (t, 1H), 7.06 (t, 1H), 6.94 (d, 2H), 6.89 (s, 1H), 5.72 (s, 2H), 4.13 (t, 2H), 4.11 (t, 2H), 2.49 (m, 2H). Mass spec; (ES−) m/z 571.2. Elemental analysis; Calculated for $C_{33}H_{27}F_3N_2O_4$: C, 69.22; H, 4.75; N, 4.89. Found: C, 69.04; H, 4.55; N, 4.82.

Example 9

Synthesis of 2-Bromo-4-[({[(1E)-(1,2-dimethyl-1H-indol-3-yl)methylidene]amino}oxy)methyl]benzoic acid Step 1: This compound was produced using similar methods as that used in Step 4, example 6, starting with 2-bromo-4-bromomethyl-benzoic acid methyl ester (0.28 g, 0.91 mmol) and 1,2-dimethyl-1H-indole-3-carbaldehyde oxime (0.18 g, 0.96 mmol). The crude material was purified by flash chromatography through silica gel using ethyl acetate/hexanes (50/50 with 1% formic acid) followed by HPLC (65% acetonitrile in 0.1% trifluoroacetic acid solution) and one final recrystallization from ethyl acetate/hexanes to give 2-bromo-4-[({[(1E)-(1,2-dimethyl-1H-indol-3-yl)methylidene]amino}oxy)methyl]benzoic acid (0.16 g, 45%) as a white solid. mp=165-166° C. $^1$H NMR (400 MHz, DMSO-d6); δ 13.34 (bs, 1H), 8.53 (s, 1H), 7.88 (d, 1H), 7.78 (s, 1H), 7.75 (d, 1H), 7.51 (d, 1H), 7.44 (d, 1H), 7.16 (t, 1H), 7.08 (t, 1H), 5.17 (s, 2H), 3.67 (s, 3H), 2.47 (s, 3H). Mass spec; (ES+) m/z 401.1, (ES−) m/z 399.0. Elemental analysis; Calculated for $C_{19}H_{17}BrN_2O_3$: C, 56.87; H, 4.27; N, 6.98. Found: C, 56.84; H, 4.3; N, 6.92.

Example 10

Screening for PAI-1 inhibition. Test compounds are dissolved in DMSO at a final concentration of 10 mM, then diluted 100× in physiologic buffer. The inhibitory assay is initiated by the addition of the test compound (1-100 μM final concentration, maximum DMSO concentration of 0.2%) in a pH 6.6 buffer containing 140 nM recombinant human plasminogen activator inhibitor-1 (PAI-1; Molecular Innovations, Royal Oak, Mich.). Following a 1 hour incubation at room temperature, 70 nM of recombinant human tissue plasminogen activator (tPA) is added, and the combination of the test compound, PAI-1 and tPA is incubated for an additional 30 minutes. Following the second incubation, Spectrozyme-tPA (American Diagnostica, Greenwich, Conn.), a chromogenic substrate for tPA, is added and absorbance read at 405 nm at 0 and 60 minutes. Relative PAI-1 inhibition is equal to the residual tPA activity in the presence of the test compounds and PAI-1. Control treatments include the complete inhibition of tPA by PAI-1 at the molar ratio employed (2:1), and the absence of any effect of the test compound on tPA alone.

Example 11

Assay for determining the IC$_{50}$ of inhibition of PAI-1. This assay is based upon the non-SDS dissociable interaction between tPA and active PAI-1. Assay plates are initially coated with human tPA (10 μg/ml). Test compounds are dissolved in DMSO at 10 mM, then diluted with physiologic buffer (pH 7.5) to a final concentration of 1-50 μM. The test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the test compound/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (Molecular Innovations, Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at OD405 nm. The quantitation of active PAI-1 bound to tPA at varying concentrations of the test compound is used to determine the IC$_{50}$. Results are analyzed using a logarithmic best-fit equation. The assay sensitivity is 5 ng/ml of human PAI-1 as determined from a standard curve ranging from 0-100 ng/ml.

Representative compounds of the present invention inhibited Plasminogen Activator Inhibitor-1 as summarized in Table I.

TABLE 1

| Compound No. | Compound Name | IC$_{50}$ (μM) | % Inhibition @ 25 μM |
|---|---|---|---|
| 1 | 4-[3-({[(1E)-(1-benzyl-1H-indol-3-yl)methylidene]amino}oxy)propoxy]-2-[(4-tert-butylbenzoyl)amino]benzoic acid | 11.81 | — |
| 2 | 4-[3-({[(1E)-(1-benzyl-1H-indol-3-yl)methylidene]amino}oxy)propoxy]-2-hydroxybenzoic acid | 21.61 | — |
| 3 | 4-[({[(1E)-(1-benzyl-1H-indol-3-yl)methylidene]amino}oxy)methyl]-2-bromobenzoic acid | 29.21 | — |
| 4 | 4-[({[(1E)-(1-benzyl-1H-indol-2-yl)methylidene]amino}oxy)methyl]-2-bromobenzoic acid | 12.33 | — |
| 5 | 4-[3-({[(1E)-(1-benzyl-1H-indol-2-yl)methylidene]amino}oxy)propoxy]-2-hydroxybenzoic acid | 22.37 | — |
| 6 | 6-[3-({[(1E)-(1-benzyl-1H-indol-3-yl)methylidene]amino}oxy)propoxy]-4'-(trifluoromethyl)-1,1'-biphenyl-3-carboxylic acid | — | 55 |
| 7 | {4-[3-({[(1E)-(1,2-dimethyl-1H-indol-3-yl)methylidene]amino}oxy)propoxy]phenyl}acetic acid | — | 54 |
| 8 | 6-[3-({[(1E)-(1-benzyl-1H-indol-2-yl)methylidene]amino}oxy)propoxy]-4'-(trifluoromethyl)-1,1'-biphenyl-3-carboxylic acid | — | 100 |
| 9 | 2-bromo-4-[({[(1E)-(1,2-dimethyl-1H-indol-3-yl)methylidene]amino}oxy)methyl]benzoic acid | — | 34 |

$^{b}$The IC$_{50}$ was determined by a modification of the Primary Screen for PAI-1 Inhibition Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

All publications and patent documents cited above are hereby incorporated by reference in their entirety for all purposes to the same extent as if each were so individually denoted.

What is claimed is:

1. A compound of the formula:

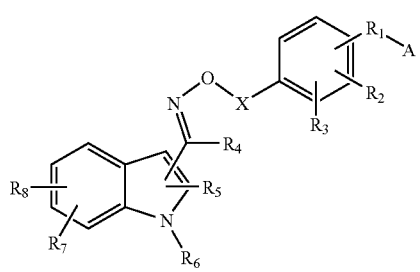

or a pharmaceutically acceptable salt or ester form thereof wherein:

$R_1$ is a direct bond to A, or $C_1$-$C_4$ alkylene or —O—$C_1$-$C_4$ alkylene, each optionally substituted with 1 to 3 substituents selected from $C_1$-$C_4$ alkyl, aryl, and benzyl;

$R_2$ and $R_3$ are, independently hydrogen, halogen, $C_1$-$C_4$ alkyl, $C_1$-$C_3$ perfluoroalkyl, —O—$C_1$-$C_3$ perfluoroalkyl, $C_1$-$C_3$ alkoxy, —OH, —NH$_2$, —NO$_2$, —O(CH$_2$)$_p$-aryl, —O(CH$_2$)$_p$-heteroaryl, aryl, heteroaryl, —NH(CH$_2$)$_p$-aryl, —NH(CH$_2$)$_p$-heteroaryl, —NH(CO)-aryl, —NH(CO)-heteroaryl, —O(CO)-aryl, —O(CO)-heteroaryl, —NH(CO)—CH=CH-aryl, or —NH(CO)—CH=CH-heteroaryl;

p is an integer from 0-6;

$R_4$ is hydrogen, $C_1$-$C_8$ alkyl, or $C_3$-$C_6$ cycloalkyl;

A is —COOH, tetrazole, tetronic acid, acyl tetronic acid, or a group of the formula:

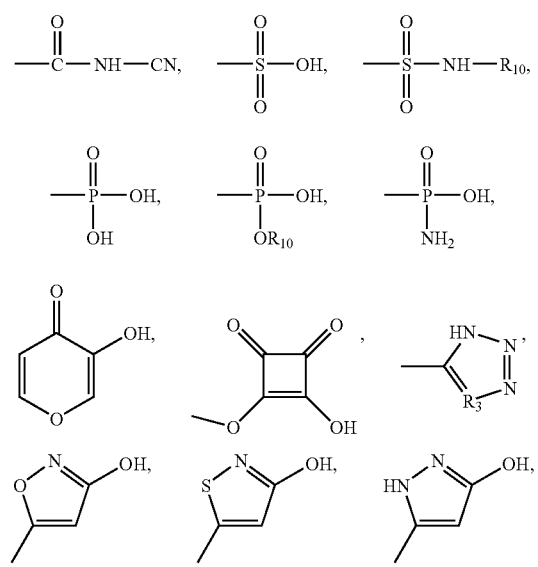

-continued

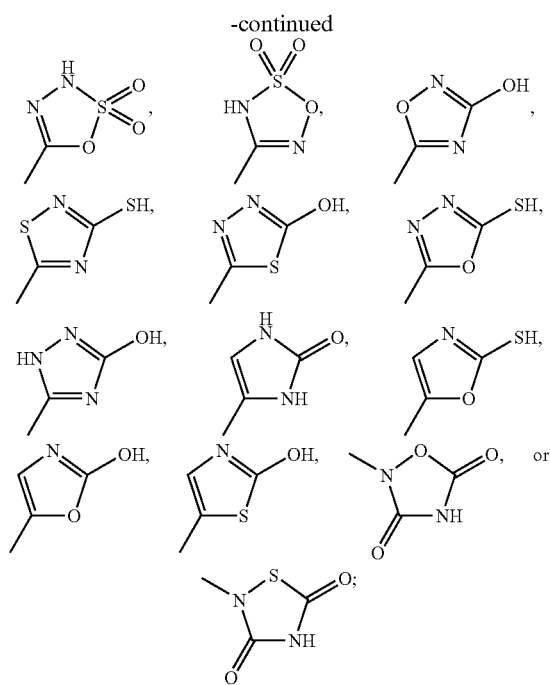

$R_{10}$ is $C_1$-$C_6$ alkyl, $C_2$-$C_6$ alkenyl, $C_3$-$C_6$ cycloalkyl, -CH$_2$-($C_3$-$C_6$ cycloalkyl), $C_3$-$C_6$ cycloalkenyl, -CH$_2$-($C_3$-$C_6$ cycloalkenyl), aryl, heteroaryl, aryl($C_1$-$C_6$)alkyl, or heteroaryl($C_1$-$C_6$)alkyl;

X is $C_1$-$C_8$ alkylene, $C_3$-$C_6$ cycloalkylene, —(CH$_2$)$_m$O—, or —(CH$_2$)$_m$NH—;

m is an integer from 1-6; and $R_5$ is hydrogen, $C_1$-$C_8$ alkyl, $C_3$-$C_6$ cycloalkyl, —CH$_2$—$C_3$-$C_6$ cycloalkyl, heteroaryl, —CH$_2$-heteroaryl, aryl or benzyl;

$R_6$ is $C_1$-$C_8$ alkyl, $C_3$-$C_6$ cycloalkyl, —CH$_2$—$C_3$-$C_6$ cycloalkyl, —(CH$_2$)$_q$—CH=CH$_2$, —(CH$_2$)$_q$—CH=CH-alkyl, —(CH$_2$)$_q$—CH=C-dialkyl, —(CH$_2$)$_q$C≡CH, —(CH$_2$)$_q$C≡C-alkyl, —(CH$_2$)$_q$-alkyl, —(CH$_2$)$_q$-heteroaryl, —CO-aryl, —CO-heteroaryl, —CO-alkyl, —SO$_2$alkyl, —SO$_2$-aryl, or —SO$_2$-heteroaryl;

q is an integer from 0 to 6;

$R_7$ and $R_8$, are, independently, hydrogen, halogen, $C_1$-$C_6$ alkyl, $C_1$-$C_6$ perfluoroalkyl, —O—$C_1$-$C_6$ perfluoroalkyl, $C_1$-$C_6$ alkoxy, —OH, —NH$_2$, —NO$_2$, —O(CH$_2$)$_n$ -aryl, —O(CH$_2$)$_n$-heteroaryl, aryl, or heteroaryl; and n is an integer from 0-6, wherein the alkylene, —O-alkylene, alkyl, aryl, heteroaryl and cycloalkyl are each optionally substituted by one or more substituents.

2. A compound as claimed in claim 1, or a pharmaceutically acceptable salt or ester form thereof, wherein $R_5$ is hydrogen, $C_1$-$C_8$ alkyl, $C_3$-$C_6$ cycloalkyl, —CH$_2$—$C_3$-$C_6$ cycloalkyl, pyridinyl, —CH$_2$-pyridinyl, phenyl or benzyl wherein the rings of the cycloalkyl, pyridinyl, and benzyl groups are substituted by 1 to 3 groups selected from halogen, $C_1$-$C_6$ alkyl, $C_3$-$C_6$ cycloalkyl, $C_1$-$C_3$ perfluoroalkyl, —O—$C_1$-$C_3$ perfluoroalkyl, $C_1$-$C_3$ alkoxy, —OH, —NH$_2$, —NO$_2$ or —CN.

3. A compound as claimed in claim 1, or a pharmaceutically acceptable salt or ester form thereof, wherein $R_1$ is a direct bond.

4. A compound as claimed in claim 1, or a pharmaceutically acceptable salt or ester form thereof, wherein X is —(CH$_2$)$_m$O—.

5. A compound as claimed in claim 1, or a pharmaceutically acceptable salt or ester form thereof, wherein $R_1$ is $C_1$-$C_4$ alkylene, or —O—$C_1$-$C_4$ alkylene, each optionally substituted by 1 to 3 groups selected from $C_1$-$C_4$ alkyl, aryl, or benzyl.

6. A compound as claimed in claim 1, or a pharmaceutically acceptable salt or ester form thereof, wherein the rings of the aryl and heteroaryl groups are optionally substituted by 1 to 3 groups selected from halogen, $C_1$-$C_6$ alkyl, $C_1$-$C_3$ perfluoroalkyl, —O—$C_1$-$C_3$ perfluoroalkyl, $C_1$-$C_3$ alkoxy, —OH, —NH$_2$, —CN or —NO$_2$.

7. A compound as claimed in claim 1, or a pharmaceutically acceptable salt or ester form thereof, wherein $R_2$ is hydrogen, —OH, halogen, phenyl substituted with CF$_3$, or —NH(CO)-aryl wherein the aryl group is unsubstituted or substituted with t-butyl.

8. A compound as claimed in claim 1, or a pharmaceutically acceptable salt or ester form thereof, wherein $R_3$ is hydrogen, —OH, halogen, phenyl substituted with CF$_3$, or —NH(CO)-aryl wherein the aryl group is unsubstituted or substituted with t-butyl.

9. A compound as claimed in claim 1, or a pharmaceutically acceptable salt or ester form thereof, wherein $R_4$ is hydrogen.

10. A compound as claimed in claim 1, or a pharmaceutically acceptable salt or ester form thereof, wherein $R_5$ is hydrogen or $C_1$-$C_8$ alkyl and $R_7$ and $R_8$ are independently selected from hydrogen or $C_1$-$C_6$ alkyl.

11. A compound as claimed in claim 1, or a pharmaceutically acceptable salt or ester form thereof, wherein $R_6$ is benzyl.

12. A compound as claimed in claim 1 wherein A is tetrazole.

13. A compound of claim 1, having the formula:

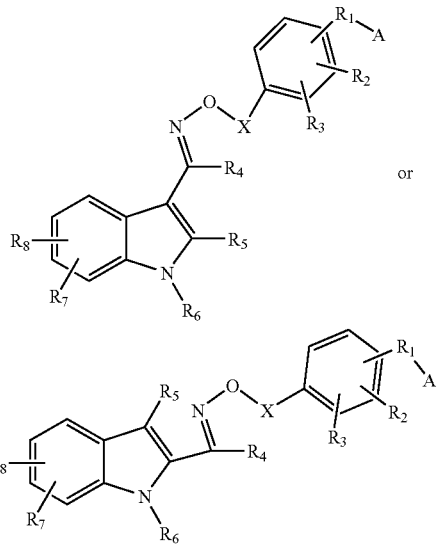

or a pharmaceutically acceptable salt or ester form thereof.

14. A compound of claim 1, having the formula:

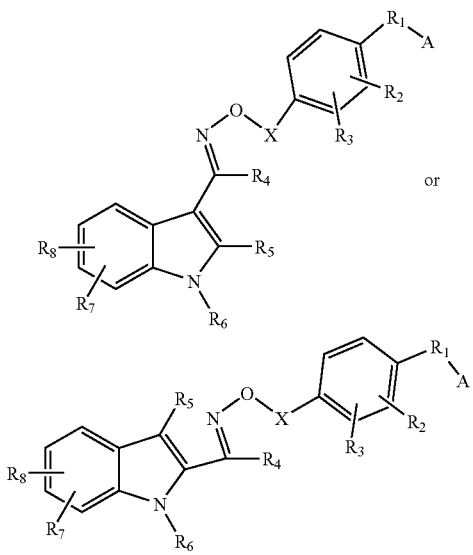

or a pharmaceutically acceptable salt or ester form thereof.

15. A compound of claim 1, having the formula:

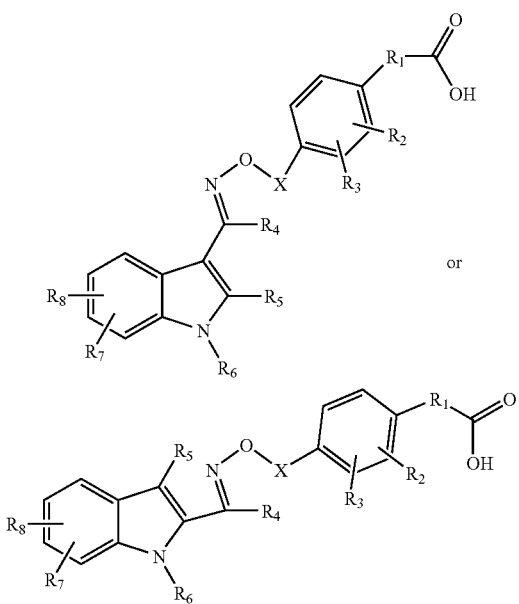

or a pharmaceutically acceptable salt or ester form thereof.

16. The compound of claim 1 that is 4-[3-({[(1E)-(1-benzyl-1H-indol-3-yl)methylidene]amino}oxy)propoxy]-2-[(4-tert-butylbenzoyl)amino]benzoic acid or a pharmaceutically acceptable salt or ester form thereof 4-[3-({[(1E)-(1-benzyl-1H-indol-3-yl)methylidene]amino}oxy)propoxy]-2-hydroxybenzoic acid or a pharmaceutically acceptable salt or ester form thereof; 4-[({[(1E)-(1-benzyl-1H-indol-3-yl)methylidene]amino}oxy)methyl]-2-bromobenzoic acid or a pharmaceutically acceptable salt or ester form thereof; 4-[({[(1E)-(1-benzyl-1H-indol-2-yl)methylidene]amino}oxy)methyl]-2-bromobenzoic acid or a pharmaceutically acceptable salt or ester form thereof or 4-[3-({[(1E)-(1-benzyl-1H-indol-2-yl)methylidene]amino}oxy)propoxy]-2-hydroxybenzoic acid or a pharmaceutically acceptable salt or ester form thereof.

17. The compound of claim 1 that is 6-[3-({[(1E)-(1-benzyl-1H-indol-3-yl)methylidene]amino}oxy)propoxy]-4'-(trifluoromethyl)-1,1'-biphenyl-3-carboxylic acid or a pharmaceutically acceptable salt or ester form thereof; {4-[3-({[(1E)-(1,2-dimethyl-1H-indol-3-yl)methylidene]amino}oxy)propoxy]phenyl}acetic acid or a pharmaceutically acceptable salt or ester form thereof; 6-[3-({[(1E)-(1-benzyl-1H-indol-2-yl)methylidene]amino}oxy)propoxy]-4'-(trifluoromethyl)-1,1'-biphenyl-3-carboxylic acid or a pharmaceutically acceptable salt or ester form thereof; or 2-bromo-4-[({[(1E)-(1,2-dimethyl-1H-indol-3-yl)methylidene]amino}oxy)methyl]benzoic acid or a pharmaceutically acceptable salt or ester form thereof.

18. A method of inhibiting PAI-1 activity in a subject, the method comprising administering to a subject in need thereof a therapeutically effective amount of a compound as claimed in claim 1 or a pharmaceutically acceptable salt or ester form thereof.

19. A method of claim 18, wherein the therapeutically effective amount is from 25 mg/kg/day to 200 mg/kg/day.

20. A method for treating a PAI-1 related disorder in a subject, the method comprising administering to a subject in need thereof a therapeutically effective amount of the compound as claimed in claim 1 or a pharmaceutically acceptable salt or ester form thereof.

21. A method of claim 20, wherein the therapeutically effective amount is from 25 mg/kg/day to 200 mg/kg/day.

22. A method of claim 20, wherein the PAI-1 related disorder is impairment of the fibrinolytic system.

23. A method of claim 20, wherein the PAI-1 related disorder is thrombosis, atrial fibrillation, pulmonary fibrosis, myocardial ischemia, stroke, thromboembolic complication of surgery, cardiovascular disease, atherosclerotic plaque formation, chronic obstructive pulmonary disease, renal fibrosis, polycystic ovary syndrome, diabetes, Alzheimer's disease, breast or ovarian or cancer.

24. A method of claim 23, wherein the thrombosis is selected from the group consisting of venous thrombosis, arterial thrombosis, cerebral thrombosis, and deep vein thrombosis.

25. A method of claim 23, wherein the PAI-1 related disorder is cardiovascular disease caused by noninsulin dependent diabetes mellitus in a subject.

26. A pharmaceutical composition comprising a pharmaceutically effective amount of a compound as claimed in claim 1, or a pharmaceutically acceptable salt or ester form thereof, and a pharmaceutically acceptable excipient or carrier.

27. A compound of claim 1, or a pharmaceutically acceptable salt or ester form thereof, wherein
$R_1$ is a direct bond to A or $C_1$-$C_3$ alkylene;
$R_2$ is hydrogen, halogen, $C_1$-$C_3$ alkyl, $C_1$-$C_3$ perfluoroalkyl, aryl, heteroaryl, —O—$C_1$-$C_3$ perfluoroalkyl, $C_1$-$C_3$ alkoxy, —OH, —O(CH$_2$)$_p$-aryl, —NH(CO)-aryl or —NH(CO)-heteroaryl;
$R_3$ is hydrogen, halogen, $C_1$-$C_3$ alkyl, $C_1$-$C_3$ perfluoroalkyl, aryl, heteroaryl, —O—$C_1$-$C_3$ perfluoroalkyl, $C_1$-$C_3$ alkoxy, —OH, —O(CH$_2$)$_p$-aryl, —NH(CO)-aryl or —NH(CO)-heteroaryl;
$R_4$ is hydrogen or $C_1$-$C_4$ alkyl;
$R_5$ is hydrogen, $C_1$-$C_8$ alkyl, $C_3$-$C_6$ cycloalkyl, aryl, or heteroaryl;
$R_6$ is $C_1$-$C_6$ alkyl, or (CH$_2$)$_q$-aryl;

$R_7$ is hydrogen, halogen, $C_1$-$C_6$ alkyl, $C_1$-$C_6$ perfluoroalkyl, —O—$C_1$-$C_6$ perfluoroalkyl, or $C_1$-$C_6$ alkoxy;

$R_8$ is hydrogen, halogen, $C_1$-$C_6$ alkyl, $C_1$-$C_6$ perfluoroalkyl, —O—$C_1$-$C_6$ perfluoroalkyl, or $C_1$-$C_6$ alkoxy;

A is —COOH or tetrazole; and

X is —$CH_2$—, —$CH_2$—$CH_2$—O—, or —$CH_2$—$CH_2$—$CH_2$—O—.

28. A compound of claim 1, or a pharmaceutically acceptable salt or ester form thereof, wherein $R_1$ is a direct bond to A or —$CH_3$—;

A is COOH;

$R_2$ and $R_3$ are each independently selected from hydrogen, bromo, hydroxy, 4-trifluoromethylphenyl or 4-t-butyl-phenyl-carbonylamino;

$R_4$ is hydrogen;

$R_5$ is hydrogen or methyl;

$R_6$ is methyl or benzyl;

$R_7$ and $R_8$ are each hydrogen; and

X is —$CH_2$— or —$CH_2$—$CH_2$—$CH_2$—O—.

* * * * *